US012576016B2

(12) United States Patent
Bossant et al.

(10) Patent No.: US 12,576,016 B2
(45) Date of Patent: Mar. 17, 2026

(54) COMPOSITION CONTAINING 4-(3-ETHOXY-4-HYDROXYPHENYL)BUTAN-2-ONE, A PRESERVATIVE AND/OR ANTIOXIDANT, A SURFACTANT AND A POLYMER, AND THE METHOD FOR PROCESSING KERATIN MATERIALS FROM THE COMPOSITION

(71) Applicant: L'OREAL, Paris (FR)

(72) Inventors: Isabelle Bossant, Chevilly Larue (FR); Sonia Eyraud, Chevilly Larue (FR)

(73) Assignee: L'OREAL, Paris (FR)

( * ) Notice: Subject to any disclaimer, the term of this patent is extended or adjusted under 35 U.S.C. 154(b) by 835 days.

(21) Appl. No.: 17/781,428

(22) PCT Filed: Dec. 2, 2020

(86) PCT No.: PCT/EP2020/084343
§ 371 (c)(1),
(2) Date: Jun. 1, 2022

(87) PCT Pub. No.: WO2021/110784
PCT Pub. Date: Jun. 10, 2021

(65) Prior Publication Data

US 2023/0093767 A1 Mar. 23, 2023

(30) Foreign Application Priority Data

Dec. 3, 2019 (FR) ...................................... 1913636

(51) Int. Cl.

| | |
|---|---|
| ***A61K 8/35*** | (2006.01) |
| ***A01N 35/02*** | (2006.01) |
| ***A61K 8/34*** | (2006.01) |
| ***A61Q 19/00*** | (2006.01) |

(52) U.S. Cl.
CPC ................ *A61K 8/35* (2013.01); *A01N 35/02* (2013.01); *A61K 8/34* (2013.01); *A61Q 19/00* (2013.01); *A61K 2800/48* (2013.01); *A61K 2800/522* (2013.01); *A61K 2800/524* (2013.01); *A61K 2800/596* (2013.01)

(58) Field of Classification Search
CPC ................................. A61K 8/35; A01N 35/02
See application file for complete search history.

(56) References Cited

U.S. PATENT DOCUMENTS

2014/0057997 A1 2/2014 Chevalier et al.
2016/0015031 A1 1/2016 Pesaro et al.

FOREIGN PATENT DOCUMENTS

| | | | | |
|---|---|---|---|---|
| FR | 2962328 A1 | 1/2012 | | |
| FR | 2962333 A1 | 1/2012 | | |
| FR | 3068206 * | 6/2017 | ............... | A61K 8/35 |
| FR | 3068205 A1 | 1/2019 | | |
| FR | 3068206 A1 | 1/2019 | | |
| FR | 3068207 A1 | 1/2019 | | |
| FR | 3068208 A1 | 1/2019 | | |
| FR | 3068210 A1 | 1/2019 | | |
| FR | 3068214 A1 | 1/2019 | | |
| FR | 3068217 A1 | 1/2019 | | |
| FR | 3070107 A1 | 2/2019 | | |
| FR | 3070108 A1 | 2/2019 | | |
| FR | 3070109 A1 | 2/2019 | | |
| FR | 3070110 A1 | 2/2019 | | |
| FR | 3070112 A1 | 2/2019 | | |
| FR | 3070113 A1 | 2/2019 | | |
| FR | 3073395 A1 | 5/2019 | | |
| JP | 2014509627 A | 4/2014 | | |
| JP | 2014172908 A | 9/2014 | | |
| WO | WO 2011/039445 A1 | 4/2011 | | |
| WO | WO2011039445 * | 4/2011 | ............... | A61K 8/37 |
| WO | WO2012130954 * | 4/2012 | ............... | A61K 8/37 |
| WO | WO 2012/130953 A1 | 10/2012 | | |
| WO | WO 2012/130954 A1 | 10/2012 | | |
| WO | WO 2012/131266 A1 | 10/2012 | | |
| WO | WO 2012/131272 A1 | 10/2012 | | |
| WO | WO2012130953 * | 10/2012 | ............... | A61K 8/35 |
| WO | WO2012131266 * | 10/2012 | ............... | A61K 8/35 |
| WO | WO2012131272 * | 10/2012 | ............... | A61K 8/35 |
| WO | WO 2016/001189 A1 | 1/2016 | | |
| WO | WO2016001189 * | 1/2016 | ............... | A61K 8/37 |
| WO | WO 2018/115058 A1 | 6/2018 | | |
| WO | WO2018115058 * | 6/2018 | ............... | A61K 8/37 |
| WO | WO 2019/002391 A1 | 1/2019 | | |
| WO | WO 2019/002392 A1 | 1/2019 | | |
| WO | WO 2019/002394 A1 | 1/2019 | | |
| WO | WO 2019/002396 A1 | 1/2019 | | |
| WO | WO 2019/002400 A1 | 1/2019 | | |
| WO | WO2019002391 * | 1/2019 | ............... | A61K 8/35 |
| WO | WO2019002392 * | 1/2019 | ............... | A61K 8/35 |
| WO | WO2019002394 * | 1/2019 | ............... | A61K 8/37 |
| WO | WO2019002396 * | 1/2019 | ............... | A61K 8/37 |
| WO | WO2019002400 * | 1/2019 | ............... | A61K 8/35 |
| WO | WO 2019/034316 A1 | 2/2019 | | |
| WO | WO 2019/105649 A1 | 6/2019 | | |
| WO | WO2019105649 * | 6/2019 | ............... | A61K 8/37 |

* cited by examiner

*Primary Examiner* — Paul V Ward
(74) *Attorney, Agent, or Firm* — POLSINELLI PC

(57) ABSTRACT

The present invention relates to a composition comprising i) at least one 4-(3-ethoxy-4-hydroxyphenyl)butan-2-one compound; ii) at least one preserving agent other than i) and/or antioxidant; iii) at least one surfactant chosen from the surfactants; iv) at least one polymer, notably a thickening polymer, which is preferably organic, and v) optionally a fatty substance. The invention also relates to the use of i) to vi) as antimicrobial agent, to a process for treating keratin materials using the composition comprising i) to vi) and to a kit comprising ingredients i) to vi).
The combination of i) ii), iii), iv) and optionally v) makes it possible to obtain an antimicrobial mixture which has excellent antimicrobial activity, in particular with respect to *Aspergillus niger, Escherichia coli, Staphylococcus aureus* and *Candida albicans*. In addition, the formulations remain stable over time while at the same time retaining antimicrobial activity over time even after 7 days, 15 days, 1 month, and at room temperature.

23 Claims, No Drawings

COMPOSITION CONTAINING 4-(3-ETHOXY-4-HYDROXYPHENYL)BUTAN-2-ONE, A PRESERVATIVE AND/OR ANTIOXIDANT, A SURFACTANT AND A POLYMER, AND THE METHOD FOR PROCESSING KERATIN MATERIALS FROM THE COMPOSITION

CROSS REFERENCE TO RELATED APPLICATIONS

This application is a National Phase filing under 35 U.S.C. § 371 of PCT/EP2020/084343 filed on 2 Dec. 2020; which application in turn claims priority to Application No. 1913636 filed in France on 3 Dec. 2019. The entire contents of each application are hereby incorporated by reference.

The present invention relates to a composition comprising i) at least one 4-(3-ethoxy-4-hydroxyphenyl)butan-2-one; ii) at least one preserving agent other than i) and/or at least one antioxidant; iii) at least one surfactant; iv) at least one polymer, notably a thickening polymer which is preferably organic, and v) optionally a fatty substance, it being understood that when the composition comprises cationic surfactants, they are in a concentration of less than 3% by weight relative to the total weight of the composition. The invention also relates to the use of i) to vi) as antimicrobial agent, to a process for treating keratin materials using the composition comprising i) to vi) and to a kit comprising ingredients i) to vi).

TECHNICAL FIELD

Microorganisms can survive and propagate in cosmetic, pharmaceutical, and food products without preserving agents. Preserving agents are regularly added to all industrial preparations intended to be stored or preserved in order to prevent microbial growth over time.

Microbial contamination during the production of an industrial product is common, even when the starting ingredients placed in said product are "clean", i.e. when no contaminating microorganisms are present. Water, for example, which is omnipresent in most cosmetic, pharmaceutical or food products, must be free of contaminating microorganisms. All other ingredients must also be screened for the presence of contaminating microorganisms. The cleanliness during production of these industrial products, the processing of the contents and the filling of the containers must be scrupulously monitored. Despite these precautions, the microbial integrity of the products may require the presence of one or more preserving agents that are compatible with the product and the stability of the composition. The products must neither allow the growth nor the viability of the contaminating microorganisms. In addition, maintaining the cleanliness during use remains problematic, since fingers, cosmetic applicators and even ambient air are not sterile. Preserving agents are therefore required in order to reduce contamination with microorganisms by consumers during normal use.

As a general rule, pathogenic microorganisms must be absent from all products sold, notably cosmetic products (Kirk Othmer Encyclopedia, Cosmetics, Martin M. Rieger, Apr. 12, 2000; https://doi.org/10.1002/0471238961.0315191318090507.a01). Over the years, preservation issues have also led to the introduction of a preserving agent with a spectrum which covers resistant contaminating microorganisms.

In addition, it appears that some of the commonly used preserving agents are inactivated by a variety of surfactants. The more hydrophobic the preserving agent, the greater the danger that it will be trapped in organized molecular systems such as micelles and subsequently become less effective or even ineffective against microorganisms, in particular pathogenic microorganisms (*Ullmann's Encyclopedia of Industrial Chemistry*, "Skin Cosmetics", G. Schneider et al., volume 33, page 221, 2012 Wiley-VCH Verlag GmbH & Co. KGaA, Weinheim DOI: 10.1002/14356007.a24_219).

It is therefore of great interest to propose new antimicrobial associations which meet these challenges.

4-(3-Ethoxy-4-hydroxyphenyl)butan-2-one or ethylzingerone (EZ) is an ingredient known as a preserving agent for compositions, notably cosmetic compositions, for protecting the compositions against microbial contamination (see, for example, WO 2011/039445). Said compound has been used alone, or as a mixture with other preserving or non-preserving compounds (see, for example, WO 2018/115058). There is great interest in being able to use this preserving agent, if possible, in a reduced concentration preferably of less than 1% by weight relative to the total weight of the composition containing it, in a composition, notably a cosmetic or pharmaceutical composition, notably a dermatological composition, which not only has an identical or even increased antimicrobial effect but which is also in compositions that are stable over time, while at the same time avoiding modification of the odor over time, and also conserving its capacity as a preserving agent, i.e. its antimicrobial efficacy. FR 1 756 156 and WO 2019/002 400 also describe cosmetic compositions comprising EZ and another preserving agent of aromatic alcohol type. These compositions do not always give a satisfactory appearance, notably in terms of a matt effect and/or a soft-focus effect after application to the skin, but also in terms of formulation stability notably with respect to temperature.

In addition, there is great interest in having a composition which comprises several antimicrobial agents, which remains stable in terms of formulation, and which is not too viscous, i.e. less than 90 poises, preferably less than 45 poises. It is also sought for the composition not to change, notably in terms of appearance and/or viscosity over time even after several weeks or even several months of storage at a temperature of greater than or equal to 25° C., notably between 37 and 45° C., and/or at a temperature below 25° C., notably between 1° C. and 10° C. such as 4° C.

Moreover, the compositions intended to be applied to keratin materials, notably the skin, must if possible have a non-glossy effect after application of the cosmetic composition, or even, if possible, a matt effect.

In terms of the sensation of the composition to be applied to keratin materials, an effect of pleasure of application that is sufficiently long, with a feel that may also be accompanied by a fresh sensation, is very often sought.

It has been discovered, unexpectedly, that the mixture below makes it possible to obtain an antimicrobial mixture which has an improvement in or even synergism of antimicrobial activity while at the same time conserving physicochemical stability of the formula over time; mixture: i) of at least one 4-(3-ethoxy-4-hydroxyphenyl)butan-2-one or an organic or mineral base salt thereof, and also solvates thereof such as hydrates; ii) of at least one preserving agent other than i) and/or at least one antioxidant; iii) of at least one surfactant; iv) of at least one thickening polymer which is preferably organic, and v) optionally of at least one fatty substance that is notably liquid at room temperature and at atmospheric pressure, it being understood that when the mixture comprises one or more cationic surfactants, they are in an amount of less than 3% by weight relative to the total weight of ingredients i) to v). Furthermore, it is seen that the composition as defined below comprising ingredients i) to iv) and optionally v) as defined previously remains stable even after several weeks or even months at room temperature or even at temperatures above 25° C. (37 and 45° C.). Moreover, it is seen that neither the combination of ingredients i) to iv) and optionally v) nor the composition shows a change in odor or an unpleasant odor which appears over time.

Moreover, the viscosity of the compositions of the invention is sufficient for good application to keratin materials and/or is stable over time. The application to keratin materials, notably the skin, is pleasant, notably with a good sensation on applying the composition with circular movements of the fingers on the skin. A pleasant fresh sensation on the skin during application may even be perceived.

A subject of the present invention is also a composition, particularly a cosmetic composition, comprising ingredients i) to iv) and optionally v) as defined previously, it being understood that said composition comprises an amount of cationic surfactants of less than 0.5% by weight relative to the total weight of the composition.

A subject of the invention is also a process for the non-therapeutic cosmetic treatment of keratin materials, comprising the application to said keratin materials, notably human keratin materials such as the skin, of a composition, notably a cosmetic composition, comprising ingredients i) to iv) and optionally v) as defined previously. The process may be a cosmetic process for caring for, making up, fragrancing or cleansing keratin materials.

A subject of the invention is also a process for preserving a composition, notably comprising a physiologically acceptable medium, in particular a cosmetic or pharmaceutical composition, characterized in that it consists in incorporating into said composition an antimicrobial mixture i) to iv) and optionally v) as defined previously.

The results of the examples described below show that the antimicrobial activity of the combination of i), ii), iii) and iv), and optionally v) as defined previously is improved according to the minimum inhibitory concentration (MIC) measurements taken with several mixtures compared with i) alone or ii) alone in an equivalent amount.

The combination of i) ii), iii), iv) and optionally v) makes it possible to obtain an antimicrobial mixture which has excellent antimicrobial activity, in particular with respect to *Aspergillus niger, Escherichia coli, Staphylococcus aureus* and *Candida albicans*. In addition, the compositions remain stable over time while at the same time retaining antimicrobial activity over time even after 7 days, 15 days or 1 month, and at room temperature.

More precisely, a subject of the invention is an antimicrobial mixture comprising, or constituted of (or consisting of), i), ii), iii) and iv) and optionally v) as defined previously, the combination from 80% to 90% by weight relative to the total weight of said combination.

For the purposes of the present invention and unless otherwise indicated:

the term "thickening polymer" means a polymer which, when introduced at 1% by weight into an aqueous solution or an aqueous-alcoholic solution containing 30% ethanol, and at pH 7, or into an oil chosen from liquid petroleum jelly, isopropyl myristate or cyclopentadimethylsiloxane, makes it possible to achieve a viscosity of at least 100 cps and preferably of at least 500 cps, at 25° C. and at a shear rate of 1 $s^{-1}$. This viscosity may be measured using a cone/plate viscometer (Haake R600 rheometer or the like). The thickening polymers may thicken the aqueous phase and/or the fatty phase, preferentially the aqueous phase;

the term "organic thickening polymer" means a thickening polymer as defined previously, which is formed from carbon and hydrogen, and possibly nitrogen, oxygen, sulfur, halogens such as fluorine, chlorine or bromine, and also phosphorus, alkali metals such as sodium or potassium, or alkaline-earth metals such as magnesium or calcium. The organic polymers according to the invention do not comprise silicon;

according to the invention, the term "non-cellulose-based organic thickening polymer" means an organic thickening polymer not including any cellulose units;

the term "surfactant" means a "surface agent", which is a compound that is capable of modifying the surface tension between two surfaces; surfactants are amphiphilic molecules, i.e. they contain two parts of different polarity, one lipophilic and apolar, and the other hydrophilic and polar;

for the purposes of the present invention, the term "fatty substance" means an organic compound that is insoluble in water at ordinary temperature (25° C.) and at atmospheric pressure (760 mmHg) (solubility of less than 5%, preferably less than 1% and even more preferentially less than 0.1%); in addition, the fatty substances are soluble in organic solvents under the same temperature and pressure conditions, for instance in halogenated solvents such as chloroform or dichloromethane, lower alcohols such as ethanol or aromatic solvents such as benzene or toluene;

the term "organic or mineral acid salt" more particularly means salts chosen from a salt derived from i) hydrochloric acid HCl, ii) hydrobromic acid HBr, iii) sulfuric acid $H_2SO_4$, iv) alkylsulfonic acids: Alk-$S(O)_2OH$ such as methanesulfonic acid and ethanesulfonic acid; v) arylsulfonic acids: Ar—$S(O)_2OH$ such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;

the term "organic or mineral base salts" means salts of alkaline bases or agents as defined below, such as alkali metal hydroxides, such as sodium hydroxide or potassium hydroxide, aqueous ammonia, amines or alkanolamines;

the term "cationic counterion" means a cation or a cationic group derived from an organic or mineral base salt counterbalancing the anionic charge of the ingredients of formula (I') or (II'); more particularly the cationic counterion is chosen from i) alkali metals such as sodium, potassium, preferably Na, ii) alkaline-earth metals such as calcium; iii) ammonium $R_4N^+$ with R, which may be identical or different, representing a hydrogen atom, or a $(C_1\text{-}C_6)$ alkyl group optionally substituted with one or more hydroxy groups; preferably, R represents a hydrogen atom or a $(C_1\text{-}C_4)$ alkyl group such as methyl;

a hydrocarbon-based chain is "unsaturated" or a (hetero) cyclic group is "unsaturated" when it includes one or more double bonds and/or one or more triple bonds, which may be conjugated;

an "alkyl radical" is a saturated, linear or branched, $C_1$-$C_{20}$, preferably $C_1$-$C_6$, more preferentially $C_1$-$C_4$, hydrocarbon-based radical, such as methyl or ethyl;

an "alkylene radical" is an unsaturated divalent hydrocarbon-based radical as defined previously, which may contain from 1 to 4 conjugated or unconjugated double bonds —C═C—; the alkenylene group particularly contains 1 or 2 unsaturations;

the expression "optionally substituted" assigned to the alkyl radical implies that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals;

an "alkoxy radical" is an alkyl-oxy radical for which the alkyl radical is a linear or branched $C_1$-$C_{16}$, preferentially $C_1$-$C_8$, hydrocarbon-based radical; —the expression "at least one" is equivalent to "one or more";

a "heterocyclic" group is a saturated or unsaturated, aromatic or non-aromatic, monocyclic or polycyclic, hydrocarbon-based 5- to 12-membered cyclic group comprising from 1 to 5 heteroatoms chosen from oxygen, sulfur and nitrogen, forming part of at least one ring member of a ring; in particular, the heterocyclic radical is chosen from morpholinyl, piperazinyl, piperidyl, furyl, pyridyl, indolyl and (benz)imidazolyl;

a "cycloalkyl" group is a saturated or unsaturated, non-aromatic, monocyclic or polycyclic, 4- to 14-membered hydrocarbon-based group including from 4 to 14 carbon atoms, such as cyclobutyl, cyclopentyl and cyclohexyl;

an "aryl" group is an unsaturated, aromatic, monocyclic or polycyclic, 6- to 14-membered hydrocarbon-based group including from 6 to 14 carbon atoms, such as phenyl or diphenyl, preferably phenyl;

the term "inclusive" for a range of concentrations means that the limits of the range are included in the defined interval.

i) 4-(3-Ethoxy-4-hydroxyphenyl)butan-2-one is a Compound of Formula (I):

[Chem. 1]

(I)

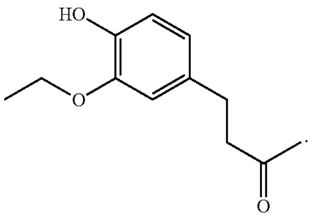

i) 4-(3-Ethoxy-4-hydroxyphenyl)butan-2-one may be found in solvated form, notably in hydrated form.

i) 4-(3-Ethoxy-4-hydroxyphenyl)butan-2-one may be found in a form salified with an organic or mineral base of formula (I') below:

[Chem. 2]

(I')

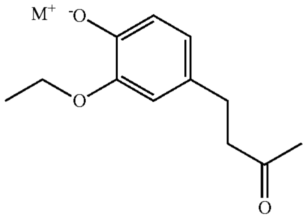

in which formula (I') $M^+$ represents a cationic counterion, in particular an alkali metal such as sodium or potassium, an alkaline-earth metal such as calcium, or an ammonium.

ii) The Preserving Agent(s) and/or the Antioxidant(s)

According to a particular embodiment of the invention, the ingredient ii) represents one or more preserving agents.

It is understood that the "preserving agent(s)" ii) are preserving agents other than i) as defined previously.

The term "preservative" or "preserving agent" means any cosmetically or pharmaceutically acceptable compound which can prevent microbial growth (or the growth of microorganisms) which may take place in cosmetic or pharmaceutical compositions, from the moment of their preparation, while they are in storage and up to the time of their conventional use by consumers. Preserving agents that may notably be mentioned include the preserving agents described in Cosmetics, Kirk-Othmer Encyclopedia of Chemical Technology. John Wiley & Sons, Inc., Martin M. Rieger; 5.2 preservatives & table 3, Apr. 12, 2000, https://doi.org/10.1002/0471238961.0315191318090507.a01.

According to a particular embodiment, the preserving agent(s) are chosen from organic preserving agents bearing an aromatic group.

Preferably, the preserving agent(s) other than i) are chosen from: a) benzene-based carboxylic acids which are optionally substituted on the phenyl group with one or more groups chosen from hydroxyl, ($C_1$-$C_{10}$)alkyl and ($C_1$-$C_{10}$)alkylcarbonyl, and also the base salts thereof, notably of alkali metals and alkaline-earth metals, b) hydroxybenzoic acid esters optionally substituted on the phenyl group with one or more groups chosen from ($C_1$-$C_{10}$)alkyl such as parabens, notably methylparaben, ethylparaben, propylparaben and butylparaben, c) aromatic alcohols; preferably, the preserving agent(s) other than i) are chosen from a) and in particular benzoic acid [65-85-0] and also the base salts thereof, notably of alkali metals and alkaline-earth metals; and also salicylic acid optionally substituted with a ($C_1$-$C_5$)alkylcarbonyl group, preferably salicylic acid.

According to another embodiment, the preserving agent(s) ii) other than i) are chosen from aromatic alcohols c) such as phenoxyethanol.

According to another advantageous embodiment of the invention, the ingredient ii) represents one or more antioxidants.

The term "antioxidant" refers to any cosmetically or pharmaceutically acceptable compound which prevents or slows down the oxidation of other ingredients on contact therewith, the oxidation possibly taking place in the cosmetic or pharmaceutical compositions from the moment of their preparation, while they are in storage and up to the time of their conventional use by the consumers, notably due to the presence of atmospheric oxygen, irradiations and the in situ formation of free radicals. Antioxidants that may notably be mentioned include the antioxidants described in Cosmetics, Kirk-Othmer Encyclopedia of Chemical Technology. John Wiley & Sons, Inc., Martin M. Rieger; 5.1 antioxidant & Table 2. Free-Radical-Inhibiting Antioxidants or Reductants Useful in Cosmetics, Apr. 12, 2000 https://doi.org/10.1002/0471238961.0315191318090507.a01

Preferably, the antioxidant(s) are chosen from keto and/or carboxylic heterocyclic acid compounds such as caffeine, amino acids and hydroxylated benzene compounds optionally substituted on the phenyl ring with one or more ($C_1$-$C_4$)alkyl groups, notably chosen from benzene-based alcohols, preferably hydroxyacetophenones.

According to a preferred embodiment of the invention, the antioxidant(s) ii) are chosen from 4-hydroxyacetophenone, also known as 4-hydroxyphenylethanone, p-acetophenol, p-hydroxyphenyl methyl ketone or piceol, which is a compound of formula (II):

[Chem. 3]

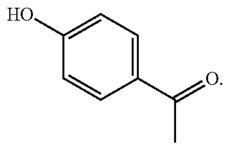

(II)

4-Hydroxyacetophenone may be in solvated form, notably in hydrated form.

4-Hydroxyacetophenone may be found in a form salified with an organic or mineral base of formula (II') below:

[Chem. 4]

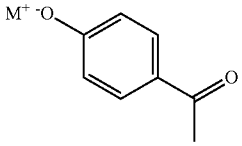

(II')

in which formula (II') $M^+$ represents a cationic counterion, in particular an alkali metal such as sodium or potassium, an alkaline-earth metal such as calcium, or an ammonium.

According to another particular embodiment of the invention, the ingredient ii) represents a mixture of one or more preserving agents and of one or more antioxidants as defined previously, in particular a mixture of a preserving agent chosen from the aromatic alcohols c) such as phenoxyethanol and an antioxidant chosen from keto and/or carboxylic heterocyclic acid compounds such as caffeine.

According to another advantageous embodiment of the invention, the ingredient ii) represents one or more compounds which are preserving agents and antioxidants.

According to a particular embodiment of the invention, i) 4-(3-ethoxy-4-hydroxyphenyl)butan-2-one and the ingredient ii), notably 4-hydroxyacetophenone, are present in said mixture or in the composition in a content such that the weight ratio i)/ii) ranges from 0.05 to 5, preferably ranges from 0.08 to 5, preferentially ranges from 0.08 to 0.25, and from 2 to 4, more preferentially ranges from 0.15 to 0.25 and from 3 to 3.8. Such a mixture has good antimicrobial activity on molds, notably on *Aspergillus niger.*

Advantageously, i) 4-(3-ethoxy-4-hydroxyphenyl)butan-2-one and the ingredient ii), notably 4-hydroxyacetophenone, are present in said mixture or in the composition in a content such that the weight ratio i)/ii) ranges from 0.08 to 0.5, preferentially ranges from 0.08 to 0.3, preferentially ranges from 0.08 to 0.25, more preferentially ranges from 0.15 to 0.25. Such a mixture has good antimicrobial activity on molds, notably on *Aspergillus niger.*

According to another particular embodiment of the invention, i) 4-(3-ethoxy-4-hydroxyphenyl)butan-2-one and the ingredient ii), notably 4-hydroxyacetophenone, are present in said mixture or in the composition in a content such that the weight ratio i)/ii) ranges from 0.5 to 5, preferentially ranges from 1 to 4 and more preferentially 3 to 3.8. Such a mixture has good antimicrobial activity on *Aspergillus niger, Escherichia coli, Staphylococcus aureus* and *Candida albicans*, and this being over time, even after several weeks (1 week, 2 weeks or even one month).

iii) The surfactant(s)

The mixture of the invention comprises the ingredients i) to iv) and optionally v) as defined previously, it being understood that when the mixture comprises one or more cationic surfactants, they are in an amount of less than 3% by weight relative to the total weight of i) to v), preferentially less than or equal to 2% by weight of cationic surfactants, more particularly less than or equal to 1% by weight of cationic surfactants relative to the total weight of the composition, even more preferentially in an amount of less than 0.5% by weight of surfactants; better still, the mixture does not comprise any cationic surfactants.

The composition of the invention comprises iii) one or more surfactants chosen from nonionic, anionic, zwitterionic or amphoteric or cationic surfactants, it being understood that the composition comprises an amount of less than 0.5% by weight relative to the total weight of the composition, preferably an amount of less than or equal to 0.2%, even more particularly less than or equal to 0.1% by weight relative to the total weight of the composition; even more preferentially, the composition comprises an amount of less than 0.05%; better still, the composition of the invention does not comprise any cationic surfactants. According to a preferred embodiment of the invention, the surfactant(s) are nonionic or anionic, preferably nonionic.

Among the nonionic surfactants according to the invention, mention may be made, alone or as mixtures, of a) fatty alcohols, b) α-diols and c) alkylphenols, these three types of compounds a) to c) being polyethoxylated, polypropoxylated and/or polyglycerolated and containing a fatty chain including, for example, 8 to 30 carbon atoms, in particular including 10 to 22 carbon atoms, the number of ethylene oxide or propylene oxide groups possibly ranging notably from 2 to 200, in particular from 10 to 100, and the number of glycerol groups possibly ranging notably from 2 to 200, in particular from 10 to 100. Mention may also be made of ethylene oxide (EO) and propylene oxide (PO) copolymers, condensates of ethylene oxide and of propylene oxide with fatty alcohols; polyethoxylated fatty amides preferably having from 2 to 30 mol of EO, polyglycerolated fatty amides including on average 1 to 5, and in particular 1.5 to 4, glycerol groups, oxyethylenated fatty acid esters of sorbitan containing from 2 to 200 mol of EO, in particular from 10 to 100 EO; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Preferably, the nonionic surfactant is chosen from: (poly)ethoxylated fatty alcohols; glycerolated fatty alcohols;

alkylpolyglycosides, preferably oxyethylenated fatty acid mono- and diesters of sorbitan containing from 2 to 200 mol of EO, in particular from 10 to 100 EO.

More preferentially, the surfactants are chosen from oxyethylenated fatty acid mono- and diesters of sorbitan containing from 2 to 200 mol of EO, in particular from 10 to 100 EO, such as propylene glycol stearate containing from 10 to 30 EO, such as 20 EO; glyceryl monostearate/distearate/polyethylene glycol stearate (100 EO).

The term "fatty chain" means a linear or branched, saturated or unsaturated, hydrocarbon-based chain comprising 6 to 30 carbon atoms, preferably from 8 to 24 carbon atoms, such as stearyl.

As regards the alkylpolyglycosides, these compounds are well known and may be represented more particularly by the following general formula: $R_1O—(R_2O)_t(G)_v$ (III) in which formula (III):

- $R_1$ represents a linear or branched alkyl and/or alkenyl radical including from about 8 to 24 carbon atoms, or an alkylphenyl radical, the linear or branched alkyl radical of which includes from 8 to 24 carbon atoms;
- $R_2$ represents an alkylene radical including from about 2 to 4 carbon atoms;
- G represents a sugar unit including from 5 to 6 carbon atoms;
- t is an integer between 0 and 10 inclusive, preferably between 0 and 4, preferably between 0 and 4; and
- v denotes an integer inclusively between 1 and 15.

Preferred alkylpolyglycosides according to the present invention are compounds of formula (III) in which $R_1$ more particularly denotes a linear or branched, saturated or unsaturated alkyl radical including from 8 to 18 carbon atoms, t denotes a value ranging from 0 to 3 and more particularly equal to 0, and G may denote glucose, fructose or galactose, preferably glucose. The degree of polymerization, i.e. the value of v in formula (III), may range from 1 to 15 and preferably from 1 to 4. The average degree of polymerization is more particularly between 1 and 2 and even more preferentially from 1.1 to 1.5.

The glycoside bonds between the sugar units are of 1-6 or 1-4 type and preferably of 1-4 type.

Compounds of formula (III) are notably represented by the products sold by the company Cognis under the names Plantaren® (600 CS/U, 1200 and 2000) or Plantacare® (818, 1200 and 2000). It is also possible to use the products sold by the company SEPPIC under the names Triton CG 110 (or Oramix CG 110) and Triton CG 312 (or Oramix® NS 10), the products sold by the company BASF under the name Lutensol GD 70 or those sold by the company Chem Y under the name AG10 LK.

It is also possible to use, for example, $(C_8/C_{16})$alkyl-1,4-polyglucoside as an aqueous 53% solution, sold by Cognis under the reference Plantacare® 818 UP.

As regards the mono- or polyglycerolated surfactants, they preferably include on average from 1 to 40 glycerol groups, more particularly from 10 to 30 glycerol groups, such as 20.

According to a particular embodiment of the invention, the surfactants are monoglycerolated or polyglycerolated and are preferably chosen from compounds having the formulae below:

$RO[CH_2CH(CH_2OH)O]_mH,$ $RO[CH_2CH(OH)CH_2O]_mH$ or $RO[CH(CH_2OH)CH_2O]_mH;$ in which formulae:

- R represents a linear or branched, saturated or unsaturated, hydrocarbon-based radical including from 8 to 40 carbon atoms and preferably from 10 to 30 carbon atoms;
- m is a number between 1 and 30, preferably between 1 and 10, more particularly from 1.5 to 6. R may optionally comprise heteroatoms, for instance oxygen and nitrogen. In particular, R may optionally comprise one or more hydroxyl and/or ether and/or amide groups. R preferably denotes optionally mono- or polyhydroxylated $C_{10}$-$C_{20}$ alkyl and/or alkenyl radicals.

Preferably, the composition of the invention comprises one or more (poly)ethoxylated fatty alcohols which are suitable for implementing the invention, more particularly chosen from alcohols including from 8 to 30 carbon atoms, and preferably from 12 to 22 carbon atoms.

The (poly)ethoxylated fatty alcohols more particularly contain one or more linear or branched, saturated or unsaturated hydrocarbon-based groups, comprising 8 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

The (poly)ethoxylated fatty alcohol(s) preferably have the following formula:

$$R^a—[O—CH_2—CH_2]_n—OH$$

with

- $R^a$ representing a linear or branched $C_1$-$C_{40}$ alkyl or linear or branched $C_2$-$C_{30}$ alkenyl (preferentially C—$C_{30}$ alkyl) group; and
- n representing an integer inclusively between 1 and 200, preferentially between 2 and 100, more particularly inclusively between 10 and 50, even more particularly inclusively between 15 and 30 inclusive, such as 100 or 20.

The (poly)ethoxylated fatty alcohols are more particularly fatty alcohols including from 8 to 22 carbon atoms and oxyethylenated with 1 to 30 mol of ethylene oxide (1 to 100 EO). Among them, mention may be made more particularly of lauryl alcohol 20 EO, lauryl alcohol 30 EO, decyl alcohol 3 EO, decyl alcohol 5 EO and oleyl alcohol 20 EO.

Mixtures of these (poly)oxyethylenated fatty alcohols may also be used.

Among the nonionic surfactants, use is preferably made of $C_6$-$C_{24}$ alkyl polyglucosides and (poly)ethoxylated fatty alcohols, and $C_8$-$C_{16}$ alkyl polyglucosides are more particularly used.

The amount of nonionic surfactants preferably ranges from 0.5% to 20% by weight, in particular from 1% to 10% by weight and more particularly from 2% to 5% by weight relative to the total weight of the composition of the invention.

According to another particular embodiment of the invention, the composition comprises one or more anionic surfactants.

The term "anionic surfactant" means a surfactant including, as ionic or ionizable groups, only anionic groups. These anionic groups are preferably chosen from the groups —C(O)OH, —C(O)O—, $—SO_3H$, $—S(O)_2O—$, $—OS(O)_2OH$, $—OS(O)_2O—$, $—P(O)_2OH$, $—P(O)_2O—$, $—P(O)O_2—$, $—P(OH)_2$, =P(O)OH, —P(OH)O—, =P(O)O—, =POH and =PO—, the anionic parts comprising a cationic counterion such as an alkali metal, an alkaline-earth metal or an ammonium, more preferentially the groups are carboxy —C(O)OH or carboxylate —C(O)O—.

As examples of anionic surfactants that may be used in the composition according to the invention, mention may be made of alkyl carboxylic acids, alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, salts of alkyl diesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts, and the corresponding non-salified forms of all these compounds, the alkyl and acyl groups of all these compounds including from 8 to 30 carbon atoms and preferably from 10 to 22 carbon atoms and the aryl group denoting a phenyl group.

These compounds may be oxyethylenated and then preferably include from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may notably be mentioned include monoethanolamine, diethanolamine and triethanolamine salts, monoisopropanolamine, diisopropanolamine and triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular sodium or magnesium salts are preferably used.

Among the anionic surfactants mentioned, it is preferred to use ($C_6$-$C_{24}$)alkyl carboxylic acids, in particular ($C_{10}$-$C_{20}$)alkyl carboxylic acids, preferably of natural origin, in particular of plant origin, such as stearic acid, which may be in the form of alkali metal, ammonium, amino alcohol and alkaline-earth metal salts, or a mixture of these compounds.

The amount of anionic surfactants preferably ranges from 0.5% to 20% by weight, in particular from 1% to 10% by weight and more particularly from 2% to 5% by weight relative to the total weight of the composition of the invention.

The amount of surfactants preferably ranges from 0.5% to 30% by weight, in particular from 1% to 20% by weight, more particularly from 2% to 10% by weight, even more particularly from 3% to 8% by weight and more preferentially between 4% and 6%, relative to the total weight of the composition of the invention.

iv) The Organic Thickening Polymer(s):

According to a particular embodiment of the invention, the composition comprises one or more thickening organic polymers.

The term "thickening polymer" means a polymer which, when introduced at 1% by weight in an aqueous solution or an aqueous-alcoholic solution containing 30% ethanol, and at pH=7, or in an oil chosen from liquid petroleum jelly, isopropyl myristate or cyclopentadimethylsiloxane, makes it possible to achieve a viscosity of at least 100 cps and preferably of at least 500 cps, at 25° C. and at a shear rate of 1 $s^{-1}$. This viscosity may be measured using a cone/plate viscometer (Haake R600 rheometer or the like). The thickening polymers may be thickeners for the aqueous phase and/or for the fatty phase, preferentially for the aqueous phase.

The term "organic" thickening polymer means a thickening polymer as defined previously, which is formed from carbon and hydrogen, and possibly nitrogen, oxygen, sulfur, halogens such as fluorine, chlorine or bromine, and also phosphorus, alkali metals such as sodium or potassium, or alkaline-earth metals such as magnesium or calcium. The organic polymers according to the invention do not comprise any silicon.

The organic thickening polymers according to the invention may be of natural or synthetic origin.

The thickening polymers may be associative or non-associative anionic, cationic, amphoteric or nonionic polymers, more particularly anionic polymers.

They may be thickeners for the aqueous or oily phases.

By way of aqueous-phase thickening polymers, mention may be made of associative or non-associative, preferably non-associative, thickening polymers, bearing sugar units.

For the purposes of the present invention, the term "sugar unit" means a unit derived from a carbohydrate of formula $C_n(H_2O)_{n-1}$ or $(CH_2O)_n$, which may be optionally modified by substitution and/or by oxidation and/or by dehydration.

The sugar units that may be included in the composition of the thickening polymers of the invention are preferably derived from the following sugars: glucose, galactose, arabinose, rhamnose, mannose, xylose, fucose, anhydrogalactose, galacturonic acid, glucuronic acid, mannuronic acid, galactose sulfate, anhydrogalactose sulfate and fructose.

Thickening polymers of the invention that may notably be mentioned include native gums such as:

a) tree or shrub exudates, including:
    acacia gum (branched polymer of galactose, arabinose, rhamnose and glucuronic acid);
    ghatti gum (polymer derived from arabinose, galactose, mannose, xylose and glucuronic acid);
    karaya gum (polymer derived from galacturonic acid, galactose, rhamnose and glucuronic acid);
    gum tragacanth (polymer of galacturonic acid, galactose, fucose, xylose and arabinose);
b) gums derived from algae, including:
    agar (polymer derived from galactose and anhydrogalactose);
    alginates (polymers of mannuronic acid and of glucuronic acid);
    carrageenans and furcellerans (polymers of galactose sulfate and of anhydrogalactose sulfate);
c) gums derived from seeds or tubers, including:
    guar gum (polymer of mannose and galactose);
    locust bean gum (polymer of mannose and galactose);
    fenugreek gum (polymer of mannose and galactose);
    tamarind gum (polymer of galactose, xylose and glucose);
    konjac gum (polymer of glucose and mannose);
d) microbial gums, including:
    xanthan gum (polymer of glucose, mannose acetate, mannose/pyruvic acid and glucuronic acid);
    gellan gum (polymer of partially acylated glucose, rhamnose and glucuronic acid);
    scleroglucan gum (glucose polymer);
e) plant extracts, including:
    cellulose (glucose polymer);
    starch (glucose polymer) and
    inulin.

These polymers may be physically or chemically modified. As physical treatment, mention may notably be made of the temperature.

As chemical treatments, mention may be made of esterification, etherification, amidation or oxidation reactions. These treatments make it possible to produce polymers that may notably be nonionic, anionic or amphoteric.

Preferably, these chemical or physical treatments are applied to guar gums, locust bean gums, starches and celluloses.

The nonionic guar gums that may be used according to the invention may be modified with $C_1$-$C_6$ (poly)hydroxyalkyl groups.

Among the $C_1$-$C_6$ (poly)hydroxyalkyl groups, mention may be made, by way of example, of hydroxymethyl, hydroxyethyl, hydroxypropyl and hydroxybutyl groups.

These guar gums are well known from the prior art and may be prepared, for example, by reacting corresponding alkene oxides, for instance propylene oxides, with the guar gum so as to obtain a guar gum modified with hydroxypropyl groups.

The degree of hydroxyalkylation preferably ranges from 0.4 to 1.2 and corresponds to the number of alkylene oxide molecules consumed by the number of free hydroxyl functions present on the guar gum.

Such nonionic guar gums optionally modified with hydroxyalkyl groups are sold, for example, under the trade names Jaguar HP8, Jaguar HP60 and Jaguar HP120 by Rhodia Chimie.

The botanical origin of the starch molecules used in the present invention may be cereals or tubers. Thus, the starches are chosen, for example, from corn starch, rice starch, cassava starch, barley starch, potato starch, wheat starch, sorghum starch or pea starch.

The starches can be chemically or physically modified, in particular by one or more of the following reactions: pregelatinization, oxidation, crosslinking, esterification, etherification, amidation or heat treatments.

Distarch phosphates or compounds rich in distarch phosphate will preferentially be used, for instance the product sold under the references Prejel VA-70-T AGGL (gelatinized hydroxypropyl cassava distarch phosphate), or Prejel TK1 (gelatinized cassava distarch phosphate) or Prejel 200 (gelatinized acetyl cassava distarch phosphate) by Avebe, or Structure Zea from National Starch (gelatinized corn distarch phosphate).

According to the invention, use may also be made of amphoteric starches, these amphoteric starches comprising one or more anionic groups and one or more cationic groups. The anionic and cationic groups may be bonded to the same reactive site of the starch molecule or to different reactive sites; they are preferably bonded to the same reactive site. The anionic groups may be of carboxylic, phosphate or sulfate type, preferably carboxylic type. The cationic groups may be of primary, secondary, tertiary or quaternary amine type.

The starch molecules may be derived from any plant source of starch, in particular such as corn, potato, oat, rice, tapioca, sorghum, barley or wheat. It is also possible to use hydrolyzates of the starches mentioned above. The starch is preferably derived from potato.

The non-associative thickening polymers of the invention may be cellulose-based polymers not including a $C_{10}$-$C_{30}$ fatty chain in their structure.

According to the invention, the term “cellulose-based polymer” means any polysaccharide compound having in its structure sequences of glucose residues linked together via β-1,4 bonds; in addition to unsubstituted celluloses, the cellulose derivatives may be anionic, cationic, amphoteric or nonionic.

Thus, the cellulose-based polymers of the invention may be chosen from unsubstituted celluloses, including those in a microcrystalline form, and cellulose ethers.

Among these cellulose-based polymers, cellulose ethers, cellulose esters and cellulose ether esters are distinguished.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates or acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the nonionic cellulose ethers not bearing a $C_{10}$-$C_{30}$ fatty chain, i.e. which are “non-associative”, mention may be made of ($C_1$-$C_4$)alkylcelluloses, such as methylcelluloses and ethylcelluloses (for example, Ethocel Standard 100 Premium from Dow Chemical); (poly)hydroxy($C_1$-$C_4$) alkylcelluloses, such as hydroxymethylcelluloses, hydroxyethylcelluloses (for example, Natrosol 250 HHR sold by Aqualon) and hydroxypropylcelluloses (for example, Klucel EF from Aqualon); mixed (poly)hydroxy($C_1$-$C_4$)alkyl-($C_1$-$C_4$)alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hydroxybutylmethylcelluloses.

Among the anionic cellulose ethers without a fatty chain, mention may be made of (poly)carboxy($C_1$-$C_4$)alkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers without a fatty chain, mention may be made of cationic cellulose derivatives such as cellulose copolymers or cellulose derivatives grafted with a water-soluble quaternary ammonium monomer, and notably described in U.S. Pat. No. 4,131,576, such as (poly) hydroxy($C_1$-$C_4$)alkylcelluloses, for instance hydroxymethyl-, hydroxyethyl- or hydroxypropylcelluloses notably grafted with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

According to one particular embodiment of the invention, the thickening polymer(s) of the invention result from the (co)polymerization of acrylate monomer $CH_2{=}C(R')—COOR'''$ (VIa) and/or from acrylamide monomer $CH_2{=}C(R')—CO—N(R'')\text{-}LY^-M^+$ (VIb); in said formulae (VIa) and (VIb), R' and R'', which may be identical or different, representing a hydrogen atom or a ($C_1$-$C_6$) alkyl group such as methyl, preferably hydrogen, R''' represents an alkali metal, an alkaline-earth metal, a hydrogen atom or a ($C_1$-$C_6$) alkyl group optionally substituted notably with one or more hydroxyl, carboxyl or amino groups; preferably, R''' represents a hydrogen atom, L representing a cyclic or acyclic, saturated or unsaturated, linear or branched, divalent hydrocarbon-based group, optionally interrupted with one or more heteroatoms such as 0 or N and comprising from 1 to 20 carbon atoms, preferably from 1 to 6 carbon atoms; preferably, L represents the group divalent —[C(R')(R")]$_p$— with p representing an integer between 1 and 4, preferably 2 and 3, such as 2, R' and R" being as defined above; more particularly, L represents —C(R')(R")—$CH_2$— or —$CH_2$—C(R')(R")— with R' and R" as defined above, and preferably R' and R" represent a ($_1$-$C_4$)alkyl group such as methyl; $Y^-$ represents an anionic group such as carboxylate, phosphate, phosphonate, sulfonate or sulfate, preferably —$S(O)_2$—O—, and $M^+$ being a cationic counterion, preferably an alkali metal, such as sodium, it being possible for said copolymer to be in a direct or inverse emulsion, preferably an inverse emulsion. More preferentially, the thickening polymer(s) of the invention result from the copolymerization of acrylate monomer $CH_2$═C(R')—COOH (VIa) and of acrylamide monomer $CH_2$═C(R')—CO—N(R")-L$Y^-M^+$ (VIb) as defined previously.

Among the non-associative thickening polymers not bearing sugar units that may be used, mention may be made of crosslinked acrylic acid or methacrylic acid homopolymers or copolymers, crosslinked 2-acrylamido-2-methylpropanesulfonic acid homopolymers and crosslinked or non-crosslinked acrylamide copolymers thereof, ammonium acrylate homopolymers, or copolymers of ammonium acrylate and of acrylamide, alone or as mixtures.

A first family of non-associative thickening polymers that is suitable for use is represented by crosslinked acrylic acid homopolymers.

Among the homopolymers of this type, mention may be made of those crosslinked with an allyl alcohol ether of the sugar series, for instance the products sold under the names Carbopol 980, 981, 954, 2984 and 5984 by the company Noveon or the products sold under the names Synthalen M and Synthalen K by the company 3 VSA.

The non-associative thickening polymers may also be crosslinked (meth)acrylic acid copolymers, such as the polymer sold under the name Aqua SF1 by the company Noveon.

The non-associative thickening polymers may be chosen from crosslinked 2-acrylamido-2-methylpropanesulfonic acid homopolymers and the crosslinked acrylamide copolymers thereof.

Among the partially or totally neutralized crosslinked copolymers of 2-acrylamido-2-methylpropanesulfonic acid and of acrylamide, mention may be made in particular of the product described in Example 1 of EP 503 853, and reference may be made to said document as regards these polymers.

The composition may similarly comprise, as non-associative thickening polymers, ammonium acrylate homopolymers or copolymers of ammonium acrylate and of acrylamide.

As examples of ammonium acrylate homopolymers, mention may be made of the product sold under the name Simulgel 600 acrylamide/sodium acryloyldimethyltaurate copolymer isohexadecane and polysorbate 80 sold by the company SEPPIC, and Microsap PAS 5193 by the company Hoechst. Among the copolymers of ammonium acrylate and of acrylamide, mention may be made of the product sold under the name Bozepol C Nouveau or the product PAS 5193 sold by the company Hoechst. Reference may notably be made to FR 2 416 723, U.S. Pat. Nos. 2,798,053 and 2,923,692 as regards the description and preparation of such compounds.

Among the aqueous-phase-thickening polymers, mention may also be made of the non-cellulose-based associative polymers that are well known to those skilled in the art and notably of nonionic, anionic, cationic or amphoteric nature.

It is recalled that "associative polymers" are polymers that are capable, in an aqueous medium, of reversibly associating with each other or with other molecules.

Their chemical structure more particularly comprises at least one hydrophilic zone and at least one hydrophobic zone.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative polymers of anionic type that may be mentioned are:

(a) those including at least one hydrophilic unit and at least one fatty-chain allyl ether unit, more particularly those of which the hydrophilic unit is constituted by an ethylenic unsaturated anionic monomer, even more particularly a vinylcarboxylic acid and most particularly an acrylic acid or a methacrylic acid or mixtures thereof.

Among these anionic associative polymers, the ones that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), notably those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

(b) those including i) at least one hydrophilic unit of unsaturated olefinic carboxylic acid type, and ii) at least one hydrophobic unit of the ($C_{10}$-$C_{30}$) alkyl ester of an unsaturated carboxylic acid type.

($C_{10}$-$C_{30}$) Alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that will be used more particularly are those constituted of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those constituted of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among said polymers above, the ones most particularly preferred according to the present invention are the products sold by the company Goodrich under the trade names Pemulen TR1®, Pemulen TR2®, Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP;

(c) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies;

(d) acrylic terpolymers comprising:

i) approximately 20% to 70% by weight of an α,β-monoethylenically unsaturated carboxylic acid [A], ii) approximately 20% to 80% by weight of an α,β-monoethylenically unsaturated non-surfactant monomer other than [A], iii) about 0.5% to 60% by weight of a nonionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion;

(e) copolymers including among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22 sold by the company Rohm & Haas, which is a methacrylic acid/ethyl acrylate/oxyalkylenated stearyl methacrylate terpolymer;

(f) amphiphilic polymers including at least one ethylenically unsaturated monomer bearing a sulfonic group, in free or partially or totally neutralized form and comprising at least one hydrophobic part. These polymers may be crosslinked or non-crosslinked. They are preferably crosslinked.

The ethylenically unsaturated monomers bearing a sulfonic group are notably chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

(Meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferentially be used.

2-Acrylamido-2-methylpropanesulfonicacid (AMPS), and also partially or totally neutralized forms thereof, will more particularly be used.

The polymers of this family may be chosen notably from random amphiphilic AMPS polymers modified by reaction with a $C_6$-$C_{22}$ n-monoalkylamine or di-n-alkylamine, and such as those described in patent application WO 00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not including a fatty chain, such as (meth)acrylic acids, pi-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described notably in patent application EP-A 750 899, U.S. Pat. No. 5,089,578 and in the following publications from Yotaro Morishima:

Self-assembling amphiphilic polyelectrolytes and their nanostructures, *Chinese Journal of Polymer Science*, Vol. 18, No. 40, (2000), 323-336;

Micelle formation of random copolymers of sodium 2-(acrylamido)-2-methylpropanesulfonate and a non-ionic surfactant macromonomer in water as studied by fluorescence and dynamic light scattering, *Macromolecules*, Vol. 33, No. 10, (2000), 3694-3704;

Solution properties of micelle networks formed by non-ionic moieties covalently bound to an polyelectrolyte: salt effects on rheological behavior—*Langmuir*, Vol. 16, No. 12, (2000) 5324-5332;

Stimuli responsive amphiphilic copolymers of sodium 2-(acrylamido)-2-methylpropanesulfonate and associative macromonomers—*Polym. Preprint, Div. Polym. Chem.* 40(2), (1999), 220-221.

Among these polymers, mention may be made of:

crosslinked or non-crosslinked, neutralized or non-neutralized copolymers, including from 15% to 60% by weight of AMPS units and from 40% to 85% by weight of ($C_8$-$C_{16}$)alkyl(meth)acrylamide or ($C_8$-$C_{16}$)alkyl(meth)acrylate units relative to the polymer, such as those described in patent application EP-A750 899;

terpolymers including from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578. Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Among the cationic associative polymers, mention may be made of:

(I) cationic associative polyurethanes;

(II) the compound sold by the company Noveon under the name Aqua CC and which corresponds to the INCI name Polyacrylate-1 Crosspolymer.

Polyacrylate-1 Crosspolymer is the product of polymerization of a monomer mixture comprising:

a di($C_1$-$C_4$ alkyl)amino($C_1$-$C_6$ alkyl) methacrylate, one or more $C_1$-$C_{30}$ alkyl esters of (meth)acrylic acid, a polyethoxylated $C_{10}$-$C_{30}$ alkyl methacrylate (20-25 mol of ethylene oxide units), a 30/5 polyethylene glycol/polypropylene glycol allyl ether, a hydroxy($C_2$-$C_6$ alkyl) methacrylate, and an ethylene glycol dimethacrylate;

(III) quaternized (poly)hydroxyethylcelluloses modified with groups including at least one fatty chain, such as alkyl, arylalkyl or alkylaryl groups including at least 8 carbon atoms, or mixtures thereof. The alkyl radicals borne by the above quaternized celluloses or hydroxyethylcelluloses preferably include from 8 to 30 carbon atoms. The aryl radicals preferably denote phenyl, benzyl, naphthyl or anthryl groups. Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18-B® ($C_{12}$ alkyl) and Quatrisoft LM-X 529-8® ($C_{18}$ alkyl) sold by the company Aqualon, and the products Crodacel QM®, Crodacel QL® ($C_{12}$ alkyl) and Crodacel QS® ($C_{18}$ alkyl) sold by the company Croda and the product Softcat SL 100® sold by the company Aqualon.

(IV) cationic polyvinyllactam polymers.

Such polymers are described, for example, in patent application WO-00/68282. As cationic poly(vinyllactam) polymers according to the invention, vinylpyrrolidone/dimethylaminopropylmethacrylamide/dodecyldimethylmethacryla midopropylammonium tosylate terpolymers, vinylpyrrolidone/dimethylaminopropylmethacrylamide/cocoyldimethylmethacrylami dopropylammonium tosylate terpolymers, vinylpyrrolidone/dimethylaminopropylmethacrylamide/lauryldimethylmethacrylamid opropylammonium tosylate or chloride terpolymers are used notably.

The amphoteric associative polymers are preferably chosen from those including at least one noncyclic cationic unit. Even more particularly, those prepared from or comprising 1 to 20 mol %, preferably 1.5 to 15 mol % and even more particularly 1.5 to 6 mol % of fatty-chain monomer relative to the total number of moles of monomers are preferred.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

The associative polymers of nonionic type that may be used according to the invention are preferably chosen from:

(a) copolymers of vinylpyrrolidone and of fatty-chain hydrophobic monomers, of which examples that may be mentioned include:

the products Antaron V216® or Ganex V216® (vinylpyrrolidone/hexadecene copolymer), sold by the company ISP, the products Antaron V220® or Ganex V220® (vinylpyrrolidone/eicosene copolymer), sold by the company ISP;

(b) copolymers of $C_1$-$C_6$ alkyl methacrylates or acrylates and of amphiphilic monomers including at least one fatty chain, for instance the oxyethylenated methyl acrylate/stearyl acrylate copolymer sold by the company Goldschmidt under the name Antil 208®;

(c) copolymers of hydrophilic methacrylates or acrylates and of hydrophobic monomers including at least one fatty chain, for instance the polyethylene glycol methacrylate/lauryl methacrylate copolymer;

(d) polyurethane polyethers including in their chain both hydrophilic blocks usually of polyoxyethylenated nature and hydrophobic blocks, which may be aliphatic sequences alone and/or cycloaliphatic and/or aromatic sequences;

(e) polymers with an aminoplast ether backbone containing at least one fatty chain, such as the Pure Thix® compounds sold by the company Sud-Chemie;

(f) celluloses or derivatives thereof, modified with groups including at least one fatty chain, such as alkyl, arylalkyl or alkylaryl groups or mixtures thereof in which the alkyl groups are of $C_8$, and in particular:

nonionic alkylhydroxyethylcelluloses such as the products Natrosol Plus Grade 330 CS and Polysurf 67 ($C_{16}$ alkyl) sold by the company Aqualon;

nonionic nonoxynylhydroxyethylcelluloses such as the product Amercell HM-1500 sold by the company Amerchol;

nonionic alkylcelluloses, such as the product Bermocoll EHM 100 sold by the company Berol Nobel;

(g) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers include at least two hydrocarbon-based lipophilic chains containing from 6 to 30 carbon atoms, separated by a hydrophilic block, the hydrocarbon-based chains possibly being side chains or chains at the end of the hydrophilic block. In particular, it is possible for one or more side chains to be envisaged. In addition, the polymer may include a hydrocarbon-based chain at one end or at both ends of a hydrophilic block.

The polyurethane polyethers may be multiblock, in particular in triblock form. The hydrophobic blocks may be at each end of the chain (for example: triblock copolymer bearing a hydrophilic central block) or distributed both at the ends and in the chain (for example, multiblock copolymer). These same polymers may also be graft polymers or star polymers.

The fatty-chain nonionic polyurethane polyethers may be triblock copolymers, the hydrophilic block of which is a polyoxyethylenated chain including from 50 to 1000 oxyethylene groups. The nonionic polyurethane polyethers include a urethane bond between the hydrophilic blocks, whence the origin of the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, use may also be made of Rheolate 205® bearing a urea function, sold by the company Rheox, or Rheolate® 208, 204 or 212, and also Acrysol RM 184®.

Mention may also be made of the product Elfacos T210® bearing a $C_{12}$-$C_{14}$ alkyl chain, and the product Elfacos T212® bearing a $C_{18}$ alkyl chain, from Akzo.

The product DW 1206B® from Rohm & Haas bearing a $C_{20}$ alkyl chain and a urethane bond, sold at a solids content of 20% in water, may also be used.

Use may also be made of solutions or dispersions of these polymers, notably in water or in aqueous-alcoholic medium. Examples of such polymers that may be mentioned include Rheolate® 255, Rheolate® 278 and Rheolate® 244 sold by the company Rheox. Use may also be made of the products DW 1206F and DW 1206J sold by the company Rohm & Haas.

The polyurethane polyethers that may be used according to the invention are in particular those described in the article by G. Fonnum, J. Bakke and Fk. Hansen—*Colloid Polym. Sci.,* 271, 380-389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold notably by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Use may also be made of fatty-phase-thickening polymers.

Preferably, the polymers for structuring the oily phase via physical interactions are chosen from polyamides, silicone polyamides, saccharide or polysaccharide mono- or polyalkyl esters, N-acylamino acid amide derivatives, and copolymers comprising an alkylene or styrene block, these copolymers possibly being diblock, triblock, multiblock or radial-block polymers, also known as star copolymers, or alternatively comb polymers.

1) Polymers Bearing at Least One Crystallizable Block in the Backbone

These are also polymers that are soluble or dispersible in the oil or a fatty phase by heating above their melting point m.p. These polymers are notably block copolymers consisting of at least two blocks of different chemical nature, one of which is crystallizable.

As polymers bearing in the backbone at least one crystallizable block that are suitable for use in the invention, mention may be made of:

i). the polymers defined in U.S. Pat. No. 5,156,911;

ii). block copolymers of olefin or of cycloolefin containing a crystallizable chain, for instance those derived from the block polymerization of:

cyclobutene, cyclohexene, cyclooctene, norbornene (i.e. bicyclo(2.2.1)hept-2-ene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a, 5,8a-octahydronaphthalene, dicyclopentadiene, and mixtures thereof;

with ethylene, propylene, 1-butene, 3-methyl-1-butene, 1-hexene, 4-methyl-1-pentene, 1-octene, 1-decene or 1-eicosene, or mixtures thereof. These block copolymers may be in particular (ethylene/norbornene) block copolymers and (ethylene/propylene/ethylidenenorbornene) block terpolymers.

Those resulting from the block copolymerization of at least 2 $C_2$-$C_{16}$, and better still $C_2$-$C_{12}$, α-olefins such as those mentioned above and in particular block bipolymers of ethylene and of 1-octene may also be used.

Copolymers containing at least one crystallizable block, the rest of the copolymer being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) of polyester type, for instance poly(alkylene terephthalate), b) of polyolefin type, for instance polyethylenes or polypropylenes;

Amorphous and lipophilic block, for instance: amorphous polyolefins or copoly(olefin)s such as poly (isobutylene), hydrogenated polybutadiene or hydrogenated poly(isoprene).

As examples of such copolymers containing a crystallizable block and an amorphous block, mention may be made of:

a) poly(δ-caprolactone)-b-poly(butadiene) block copolymers, preferably used hydrogenated, such as those described in the article "Melting behavior of poly(δ-caprolactone)-block-polybutadiene copolymers" from S. Nojima, *Macromolecules,* 32, 3727-3734 (1999), b) the hydrogenated block or multiblock poly(butylene terephthalate)-b-poly(isoprene) block copolymers cited in the article "Study of morphological and mechanical properties of PP/PBT" by B. Boutevin et al., *Polymer Bulletin,* 34, 117-123 (1995), c) the poly(ethylene)-b-copoly(ethylene/propylene) block copolymers cited in the articles "Morphology of semicrystalline block copolymers of ethylene-(ethylene-alt-propylene)" by P. Rangarajan et al., *Macromolecules,* 26, 4640-4645 (1993) and "Polymer aggregates with crystalline cores: the system poly(ethylene)poly (ethylene-propylene)" P. Richter et al., *Macromolecules,* 30, 1053-1068 25 (1997), d) the poly(ethylene)-b-poly(ethylethylene) block copolymers mentioned in the general article "Crystallization in block copolymers" by I. W. Hamley, *Advances in Polymer Science*, volume 148, 113-137 (1999).

The semicrystalline polymers that may be used in the context of the invention may be non-crosslinked or partially crosslinked, provided that the degree of crosslinking does not impede their dissolution or dispersion in the liquid oily phase by heating above their melting point. It may then be a case of chemical crosslinking, by reaction with a multifunctional monomer during the polymerization. It may also be a case of physical crosslinking, which may then be due either to the establishment of bonds of hydrogen or dipolar type between groups borne by the polymer, for instance dipolar interactions between carboxylate ionomers, these interactions being in small amount and borne by the polymer backbone, or due to a phase separation between the crystallizable blocks and the amorphous blocks borne by the polymer.

Preferably, the semicrystalline polymers that are suitable for use in the invention are non-crosslinked.

As particular examples of semicrystalline polymers that can be used in the composition according to the invention, mention may be made of the Intelimer® products from Landec described in the brochure "Intelimer® polymers". These polymers are in solid form at room temperature (25° C.). They bear crystallizable side chains and contain the monomer. Mention may notably be made of Landec IP22®, with a melting point m.p. of 56° C., which is a viscous, impermeable, non-tacky product at room temperature.

It is also possible to use the semicrystalline polymers described in Examples 3, 4, 5, 7 and 9 of U.S. Pat. No. 5,156,911, resulting from the copolymerization of acrylic acid and of $C_5$ to $C_{16}$ alkyl (meth)acrylate, such as those resulting from the copolymerization:

- of acrylic acid, of hexadecyl acrylate and of isodecyl acrylate in a 1/16/3 ratio,
- of acrylic acid and of pentadecyl acrylate in a 1/19 ratio,
- of acrylic acid, of hexadecyl acrylate and of ethyl acrylate in a 2.5/76.5/20 ratio,
- of acrylic acid, of hexadecyl acrylate and of methyl acrylate in a 5/85/10 ratio,
- of acrylic acid and of octadecyl (meth)acrylate in a 2.5/97.5 ratio.

It is also possible to use the polymer "Structure O" sold by the company National Starch, such as the product described in U.S. Pat. No. 5,736,125, of m.p. 44° C., and also semicrystalline polymers containing crystallizable side chains including fluoro groups as described in Examples 1, 4, 6, 7 and 8 of WO-A-01/19333.

It is also possible to use the semicrystalline polymers obtained by copolymerization of stearyl acrylate and of acrylic acid or of NVP, or by copolymerization of behenyl acrylate and of acrylic acid or NVP, as described in U.S. Pat. No. 5,519,063 or EP-A-0 550 745.

According to a particular embodiment variant, the semicrystalline polymers that are suitable for use in the present invention are notably alkyl acrylates, among which mention may be made of the Landec copolymers:

- Doresco IPA 13-1®: polystearyl acrylate, m.p. of 49° C. and MW of 145 000;
- Doresco IPA 13-3®: polyacrylate/methacrylic acid, m.p. of 65° C. and MW of 114000;
- Doresco IPA 13-4®: polyacrylate/vinylpyrrolidone, m.p. of 44° C. and MW of 387 000;
- Doresco IPA13-5®: polyacrylate/hydroxyethyl methacrylate, m.p. of 47° C. and MW of 397 600;
- Doresco IPA 13-6®: polybehenyl acrylate, m.p. of 66° C.

2) Non-Silicone Polyamides

The particular polyamides used in the composition according to the invention are preferably those described in U.S. Pat. No. 5,783,657 from the company Union Camp.

The section of U.S. Pat. No. 5,783,657 devoted to these polymers is incorporated by reference.

Each of these polyamides notably satisfies formula (V) below:

(V)

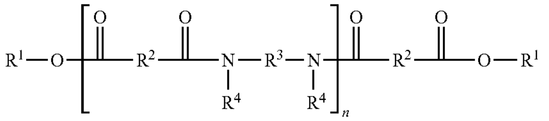

in which formula (V):

- n denotes a whole number of amide units such that the number of ester groups represents from 10% to 50% of the total number of ester and amide groups;
- $R^4$ is independently in each case an alkyl or alkenyl group containing at least 4 carbon atoms and notably from 4 to 24 carbon atoms;
- $R^2$ independently represents, in each case, a $C_4$ to $C_{55}$ hydrocarbon-based group, on condition that at least 50% of the $R^2$ groups represent a $C_{30}$ to $C_{55}$ hydrocarbon-based group;
- $R^3$ independently represents, in each case, an organic group bearing at least 2 carbon atoms, hydrogen atoms and optionally one or more oxygen or nitrogen atoms; and
- $R^4$ independently represents, in each case, a hydrogen atom, a $C_1$ to $C_{10}$ alkyl group or a direct bond to $R^3$ or to another $R^4$ so that the nitrogen atom to which both $R^3$ and $R^4$ are attached are part of a heterocyclic structure defined by $R^4$—$NR^3$, with at least 50% of $R^4$ groups representing a hydrogen atom.

In particular, the ester groups of this polyamide represent from 15% to 40% and at best from 20% to 35% of the total number of ester and amide groups. Furthermore, n advantageously represents an integer ranging from 1 to 10 and better still from 1 to 5, limits inclusive.

Preferably, $R^4$ is a $C_{12}$ to $C_{22}$ and preferably $C_{16}$ to $C_{22}$ alkyl group. Advantageously, $R^2$ may be a $C_{10}$ to $C_{42}$ hydrocarbon-based (alkylene) group. Preferably, at least 50% and better still at least 75% of the $R^2$ groups are groups containing from 30 to 42 carbon atoms. The other $R^2$ are hydrogenated $C_4$ to $C_{19}$ and preferably $C_4$ to $C_{12}$ groups. Preferably, $R^3$ represents a $C_2$ to $C_{36}$ hydrocarbon-based group or a polyoxyalkylene group and $R^4$ represents a hydrogen atom. Preferably, $R^3$ represents a $C_2$ to $C_{12}$ hydrocarbon-based group. The hydrocarbon-based groups may be linear, cyclic or branched, and saturated or unsaturated groups. Moreover, the alkyl and alkylene groups may be linear or branched, and saturated or unsaturated groups.

The thickening of the oily phase may be obtained by means of one or more polyamides defined above. In general, these polyamides are in the form of mixtures, these mixtures also possibly containing a synthetic product corresponding to a polyamide as defined above with n being 0, i.e. a diester.

As structuring polyamides that can be used in the invention, mention may also be made of polyamide resins resulting from the condensation of an aliphatic dicarboxylic acid and a diamine (including compounds containing, respectively, more than two carboxyl groups and more than two amine groups), the carboxyl and amine groups of adjacent individual units being condensed in the form of an amide bond. These polyamide resins are notably the products sold under the brand name Versamid by the companies General Mills, Inc. and Henkel Corp., under the brand name Onamid®, notably Onamid® S or C. These resins have a weight-average molecular mass ranging from 6000 to 9000. For further information regarding these polyamides, reference may be made to U.S. Pat. Nos. 3,645,705 and 3,148,125. Use is made more especially of Versamid® 30 or 744. It is also possible to use the polyamides sold or manufactured by the company Arizona under the references Uni-Rez (2658, 2931, 2970, 2621, 2613, 2624, 2665, 1554, 2623, 2662) and the product sold under the reference Macromelt 6212 by the company Henkel. For further information regarding these polyamides, reference may be made to U.S. Pat. No. 5,500,209.

As examples of structuring polyamides that can be used in the composition according to the invention, mention may also be made of the commercial products sold or manufactured by the company Arizona Chemical under the names Uniclear 80 and Uniclear 100. They are sold, respectively, in the form of an 80% (active material) gel and a 100% (active material) gel in a mineral oil. They have a softening point of from 88 to 105° C. These commercial products are a mixture of copolymers of a $C_{36}$ diacid coupled with ethylenediamine, having an average molecular mass of about 6000. The ester end groups result from the esterification of the remaining acid end groups with cetyl alcohol, stearyl alcohol or mixtures thereof (also known as cetylstearyl alcohol).

2) Saccharide or Polysaccharide Mono- or Polyalkyl Esters

Among the saccharide or polysaccharide monoalkyl or polyalkyl esters that are suitable for use in the invention, mention may be made of dextrin or inulin alkyl or polyalkyl esters.

It may notably be a dextrin monoester or polyester of at least one fatty acid notably corresponding to formula (VI) below:

(VI)

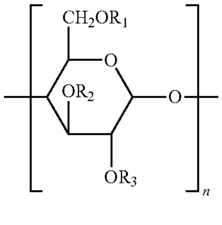

in which formula (VI):

n is an integer ranging from 3 to 200, notably ranging from 20 to 150 and in particular ranging from 25 to 50, $R_1$, $R_2$ and $R_3$, which may be identical or different, are chosen from hydrogen and an acyl group (R—C(O)—) in which the radical R is a linear or branched, saturated or unsaturated hydrocarbon-based group containing from 7 to 29, in particular from 7 to 21, notably from 11 to 19, more particularly from 13 to 17, or even 15, carbon atoms, with the proviso that at least one of said radicals $R_1$, $R_2$ or $R_3$ is other than hydrogen.

In particular, $R_1$, $R_2$ and $R_3$ may represent hydrogen or an acyl group (R—C(O)—) in which R is a hydrocarbon-based radical as defined previously, with the proviso that at least two of said radicals $R_1$, $R_2$ or $R_3$ are identical and other than hydrogen.

The radicals $R_1$, $R_2$ and $R_3$ may all contain an acyl group (R—C(O)), which may be identical or different and notably identical.

In particular, n mentioned previously advantageously ranges from 25 to 50 and is notably equal to 38 in the general formula of the saccharide ester that may be used in the present invention.

Notably, when the radicals $R_1$, $R_2$ and/or $R_3$, which may be identical or different, contain an acyl group (R—C(O)), these radicals may be chosen from caprylic, capric, lauric, myristic, palmitic, stearic, arachic, behenic, isobutyric, isovaleric, 2-ethylbutyric, ethylmethylacetic, isoheptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

Preferably, at least one dextrin palmitate is used as fatty acid ester of dextrin. This ester may be used alone or as a mixture with other esters.

Advantageously, the fatty acid ester of dextrin has a degree of substitution of less than or equal to 2.5, notably ranging from 1.5 to 2.5 and preferably from 2 to 2.5 on the basis of one glucose unit. The weight-average molecular weight of the dextrin ester may in particular be from 10 000 to 150 000, notably from 12 000 to 100 000 and even from 15 000 to 80 000.

Dextrin esters, in particular dextrin palmitates, are commercially available under the name Rheopearl TL or Rheopearl KL from the company Chiba Flour.

3) N-Acylamino Acid Amide Derivatives

The N-acylamino acid amides that may be used are, for example, diamides from the combination of an N-acylamino acid with amines comprising from 1 to 22 carbon atoms, such as those described in FR 2 281 162. They are, for example, alkylglutamic acid amide derivatives such as the laurylglutamic acid dibutylamide sold by the company Ajinomoto under the name Gelling Agent GP-1, or alternatively the 2-ethylhexylglutamic acid dibutylamide sold by the company Ajinomoto under the name Gelling Agent GA-01.

4) Copolymers Comprising an Alkylene or Styrene Block

The copolymers may have a comb or the block structure of diblock, triblock, multiblock and/or radial or startype and may include at least two thermodynamically incompatible segments.

The structuring agent may comprise, for example, a styrene segment block as described in patent applications EP 0 497 144, WO 98/42298, U.S. Pat. Nos. 6,225,690, 6,174,968 and 6,225,390, an ethylene/butylene segment or an ethylene/propylene segment as described in U.S. Pat. Nos. 6,225,690, 6,174,968 and 6,225,390, a butadiene segment, an isoprene segment, a polyvinyl segment, for instance polyalkyl (meth)acrylate or polyvinyl alcohol or polyvinyl acetate, a silicone segment as described in U.S. Pat. Nos. 5,468,477 and 5,725,882, or a combination of these segments.

A diblock copolymer is usually defined as being of A-B type in which a hard segment (A) is followed by a soft segment (B).

A triblock copolymer is usually defined as being of A-B-A type or as a ratio of a hard segment, a soft segment and a hard segment.

A multiblock, radial or star copolymer may include any type of combination of hard segments and soft segments, with the proviso that the characteristics of the hard segments and of the soft segments are conserved.

An example of hard segments of block copolymers that may be mentioned is styrene, and an example of soft segments of block copolymers that may be mentioned include ethylene, propylene and butylene, and a combination thereof.

The triblock copolymers, and notably those of polystyrene/polyisoprene or polystyrene/polybutadiene type, which are suitable for use in the invention may be those sold under the reference Luvitol HSB by the company BASF. Mention may also be made of triblock copolymers of polystyrene/copoly(ethylene-propylene) or polystyrene/copoly(ethylene-butylene) type, such as those sold under the reference Kraton by the company Shell Chemical Co., or under the reference Gelled Permethyl 99 A by the company Penreco. Such triblock copolymers are particularly preferred according to the invention.

As a further example of block copolymers that may be suitable for use in the present invention, mention may also be made of the block copolymers sold under the reference Versagel by the company Penreco, those sold under the reference Kraton by the company Shell and those sold under the reference Gel Base by the company Brooks Industries.

Among the fatty-phase thickening polymers, polymers bearing in the backbone at least one crystallizable block are preferred.

The aqueous-phase or fatty-phase thickening polymers may be used alone or as mixtures in all proportions.

Preferably, the thickeners are aqueous-phase thickeners.

Preferably, the polymers in the cosmetic compositions in accordance with the present invention advantageously have in solution or in dispersion, at 1% active material in water, a viscosity, measured using a Rheomat RM 180 rheometer at 25° C., of greater than 0.1 ps and even more advantageously greater than 0.2 cp, at a shear rate of 200 $s^{-1}$. According to a preferred embodiment of the invention, the thickening polymer(s) of the invention are non-associative and preferentially result from the (co)polymerization of acrylate monomer $CH_2$═C(R')—COOR''' (VIa) and/or from acrylamide monomer $CH_2$═C(R')—CO—N(R'')-L-$Y^-M^+$ (VIb); in said formulae (VIa) and (VIb), R' and R'', which may be identical or different, represent a hydrogen atom or a ($C_1$-$C_6$) alkyl group such as methyl, preferably hydrogen, R''' represents an alkali metal, an alkaline-earth metal, a hydrogen atom or a ($C_1$-$C_6$) alkyl group which is optionally substituted notably with one or more hydroxyl, carboxyl or amino groups, L representing a cyclic or acyclic, saturated or unsaturated, linear or branched, divalent hydrocarbon-based group, optionally interrupted and/or substituted with one or more heteroatoms such as 0 or N and comprising from 1 to 20 carbon atoms, preferably from 1 to 6 carbon atoms; preferably, L represents the divalent group —$[C(R')(R'')]_p$— with p representing an integer between 1 and 4, preferably 2 and 3, such as 2, R' and R'' being as defined previously; more particularly, L represents —C(R')(R'')—$CH_2$— or —$CH_2$—C(R')(R'')— with R' and R'' as defined previously; preferably, R' and R'' represent a ($_1$-$C_4$)alkyl group such as methyl; Y— represents an anionic group such as carboxylate, phosphate, phosphonate, sulfonate or sulfate, preferably —$S(O)_2$—O—, and $M^+$ being a cationic counterion, preferably an alkali metal, such as sodium, it being possible for said copolymer to be in a direct or inverse emulsion, preferably an inverse emulsion. More preferentially, the thickening polymer(s) of the invention result from the copolymerization of acrylate monomer $CH_2$═C(R')—COOH (VIa) and of acrylamide monomer $CH_2$═C(R')—CO—N(R'')-L-$Y^-M^+$ (VIb) as defined previously. Among the thickening polymers, mention may be made of the following; preferably the organic thickening polymers are chosen from crosslinked or non-crosslinked acrylic acid or methacrylic acid copolymers, crosslinked or non-crosslinked 2-acrylamido-2-methylpropanesulfonic acid homopolymers and crosslinked or non-crosslinked acrylamide copolymers thereof, ammonium acrylate homopolymers, or copolymers of ammonium acrylate and of acrylamide, alone or as mixtures.

According to an advantageous variant, the composition of the invention comprises one or more associative or non-associative thickening polymers, preferably non-associative, comprising sugar units in particular derived from the following sugars: glucose; galactose; arabinose; rhamnose; mannose; xylose; fucose; anhydrogalactose; galacturonic acid; glucuronic acid; mannuronic acid; galactose sulfate; anhydrogalactose sulfate and fructose, preferably anhydrogalactose galactose, preferably agar.

Preferably, the organic thickening polymer(s) are present in the composition according to the invention in a content ranging from 0.01% to 10% by weight and more preferentially from 0.1% to 5% by weight relative to the total weight of the composition.

According to a particular embodiment, the fatty substance/surfactant(s) weight ratio is inclusively between 5 and 20, preferably between 8 and 15, even more preferentially between 10 and 13, such as 11.8.

According to one embodiment of the invention, the weight ratio of the fatty substance/sum of surfactant(s) and polymer(s) [surfactant(s)+polymer] is inclusively between 0.8 and 10, particularly between 1 and 5, more particularly between 1.5 and 2.5, such as 1.8 or 1.9, preferably 1.9.

v) The Fatty Substance(s)

According to a particular embodiment of the invention, the composition of the invention also comprises v) one or more fatty substances. In particular, the fatty substance(s) of the invention are not oxyalkylenated.

Preferably, the fatty substances of the invention are chosen from hydrocarbons, fatty alcohols, fatty esters, silicones and fatty ethers, or mixtures thereof.

The fatty substances of the invention may be liquid or non-liquid at room temperature (25° C.) and at atmospheric pressure (760 mmHg; i.e. $1.013\times10^5$ Pa).

The liquid fatty substances of the invention preferably have a viscosity of less than or equal to 2 Pa·s, better still less than or equal to 1 Pa·s and even better still less than or equal to 0.1 Pa·s at a temperature of 25° C. and at a shear rate of 1 $s^{-1}$.

The term "liquid hydrocarbon" means a hydrocarbon composed solely of carbon and hydrogen atoms, which is liquid at ordinary temperature (25° C.) and at atmospheric pressure (760 mmHg; i.e. $1.013\times10^5$ Pa).

More particularly, the liquid hydrocarbons are chosen from:

- linear or branched, optionally cyclic, $C_6$-$C_{16}$ alkanes. Examples that may be mentioned include hexane, undecane, dodecane, tridecane, and isoparaffins, for instance isohexadecane, isododecane and isodecane;
- linear or branched hydrocarbons of mineral, animal or synthetic origin, containing more than 16 carbon atoms, such as liquid paraffins, liquid petroleum jelly, polydecenes, hydrogenated polyisobutene such as Parleam®, and squalane.

In a preferred variant, the liquid hydrocarbon(s) are chosen from liquid paraffins and liquid petroleum jelly.

The term "liquid fatty alcohol" means a non-glycerolated and non-oxyalkylenated fatty alcohol which is liquid at standard temperature (25° C.) and at atmospheric pressure (760 mmHg; i.e. $1.013\times10^5$ Pa).

Preferably, the liquid fatty alcohols of the invention include from 8 to 30 carbon atoms, more preferentially $C_{10}$-$C_{22}$, even more preferentially $C_{14}$-$C_{20}$, better still $C_{16}$-$C_{18}$.

The liquid fatty alcohols of the invention may be saturated or unsaturated.

The saturated liquid fatty alcohols are preferably branched. They may optionally comprise in their structure at least one aromatic or non-aromatic ring. Preferably, they are acyclic.

More particularly, the liquid saturated fatty alcohols of the invention are chosen from octyldodecanol, isostearyl alcohol or 2-hexyldecanol.

According to another variant of the invention, the fatty substance(s) are chosen from liquid unsaturated fatty alcohols. These unsaturated liquid fatty alcohols contain in their structure at least one double or triple bond. Preferably, the fatty alcohols of the invention have, in their structure, one or more double bonds. When several double bonds are present, there are preferably two or three of them, and they may be conjugated or non-conjugated.

These unsaturated fatty alcohols may be linear or branched.

They may optionally comprise in their structure at least one aromatic or non-aromatic ring. Preferably, they are acyclic.

More particularly, the unsaturated liquid fatty alcohols of the invention are chosen from oleyl alcohol, linoleyl alcohol, linolenyl alcohol or undecylenyl alcohol.

Oleyl alcohol is most particularly preferred.

The term "liquid fatty ester" means an ester that is derived from a fatty acid and/or from a fatty alcohol and that is liquid at ordinary temperature (25° C.) and at atmospheric pressure (760 mmHg; i.e. $1.013\times10^5$ Pa).

The esters are preferably liquid esters of saturated or unsaturated and linear or branched $C_1$-$C_{26}$ aliphatic mono- or polyacids and of saturated or unsaturated and linear or branched $C_1$-$C_{26}$ aliphatic mono- or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate, isostearyl neopentanoate, and $C_{10}$-$C_{22}$ and preferably $C_{12}$-$C_{20}$ alkyl (iso)stearates such as isopropyl isostearate.

Use may also be made of esters of $C_4$-$C_{22}$ di- or tricarboxylic acids and of $C_1$-$C_{22}$ alcohols and esters of mono-, di- or tricarboxylic acids and of non-sugar di-, tri-, tetra- or pentahydroxy $C_4$-$C_{26}$ alcohols.

Mention may notably be made of diethyl sebacate, diisopropyl sebacate, bis(2-ethylhexyl) sebacate, diisopropyl adipate, di-n-propyl adipate, dioctyl adipate, bis(2-ethylhexyl) adipate, diisostearyl adipate, bis(2-ethylhexyl) maleate, triisopropyl citrate, triisocetyl citrate, triisostearyl citrate, glyceryl trilactate, glyceryl trioctanoate, trioctyldodecyl citrate, trioleyl citrate, neopentyl glycol diheptanoate, and diethylene glycol diisononanoate.

The composition can also comprise, as liquid fatty ester, sugar esters and diesters of $C_6$-$C_{30}$, preferably $C_{12}$-$C_{22}$, fatty acids. It is recalled that the term "sugar" refers to oxygen-bearing hydrocarbon-based compounds bearing several alcohol functions, with or without aldehyde or ketone functions, and which include at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, notably alkyl derivatives, such as methyl derivatives, for instance methylglucose.

The sugar esters of fatty acids may be notably chosen from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, notably, oleopalmitate, oleostearate and palmitostearate mixed esters.

More particularly, use is made of monoesters and diesters and notably sucrose, glucose or methylglucose monooleate or dioleate, stearate, behenate, oleopalmitate, linoleate, linolenate or oleostearate.

An example that may be mentioned is the product sold under the name Glucate® DO by the company Amerchol, which is a methylglucose dioleate.

Finally, use may also be made of natural or synthetic glycerol esters of mono-, di- or triacids.

Among these, mention may be made of plant oils.

As oils of plant origin or synthetic triglycerides that may be used in the composition of the invention as liquid fatty esters, examples that may be mentioned include:

- triglyceride oils of plant or synthetic origin, such as liquid fatty acid triglycerides including from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, *macadamia* oil, arara oil, castor oil, avocado oil, caprylic/capric acid triglycerides, for instance those sold by the company Stearinerie Dubois or those sold under the names Miglyol® 810, 812 and 818 by the company Dynamit Nobel, jojoba oil and shea butter oil;

Preferably, liquid fatty esters resulting from monoalcohols will be used as esters according to the invention.

Isopropyl myristate or isopropyl palmitate are preferred.

The term "liquid silicone" means an organopolysiloxane that is liquid at ordinary temperature (25° C.) and at atmospheric pressure (760 mmHg; i.e. $1.013\times10^5$ Pa).

Preferably, the silicone is chosen from liquid polydialkylsiloxanes, notably liquid polydimethylsiloxanes (PDMSs), and liquid polyorganosiloxanes including at least one aryl group.

These silicones may also be organomodified. The organomodified silicones that may be used in accordance with the invention are liquid silicones as defined previously and including in their structure one or more organofunctional groups attached via a hydrocarbon-based group.

Organopolysiloxanes are defined in greater detail in Walter Noll's *Chemistry and Technology of Silicones* (1968), Academic Press. They may be volatile or nonvolatile.

When they are volatile, the silicones are more particularly chosen from those with a boiling point of between 60° C. and 260° C., and even more particularly from:

(i) cyclic polydialkylsiloxanes including from 3 to 7 and preferably from 4 to 5 silicon atoms. These are, for example, octamethylcyclotetrasiloxane notably sold under the name Volatile Silicone® 7207 by Union Carbide or Silbione® 70045 V2 by Rhodia, decamethylcyclopentasiloxane sold under the name Silicone Volatile® 7158 by Union Carbide, Silbione® 70045 V5 by Rhodia, and dodecamethylcyclopentasiloxane sold under the name Silsoft 1217 by Momentive Performance Materials, or cyclohexadimethylsiloxane, and also mixtures thereof.

Mention may also be made of cyclocopolymers of the dimethylsiloxane/methylalkylsiloxane type, such as Silicone Volatile® FZ 3109 sold by the company Union Carbide, of formula:

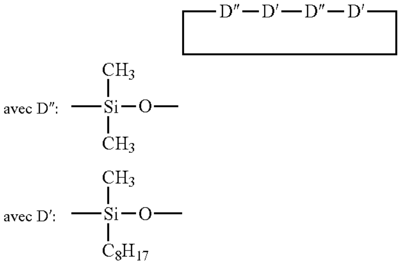

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ $m^2/s$ at 25° C. An example is decamethyltetrasiloxane notably sold under the name SH 200 by the company Toray Silicone. Silicones falling within this category are also described in the article published in Cosmetics and Toiletries, Vol. 91, January 76, pages 27-32—Todd & Byers Volatile Silicone Fluids for Cosmetics. The viscosity of the silicones is measured at 25° C. according to the standard ASTM 445 Appendix C.

Nonvolatile polydialkylsiloxanes may also be used.

These nonvolatile silicones are more particularly chosen from polydialkylsiloxanes, among which mention may be made mainly of polydimethylsiloxanes bearing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200, with a viscosity of 60 000 $mm^2/s$;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from Rhodia.

Among the silicones containing aryl groups are polydiarylsiloxanes, notably polydiphenylsiloxanes and polyalkylarylsiloxanes. Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF1250 and SF1265.

The organomodified liquid silicones may notably contain polyethyleneoxy and/or polypropyleneoxy groups. Mention may thus be made of the silicone KF-6017 sold by Shin-Etsu, and the oils Silwet® L722 and L77 from the company Union Carbide.

The liquid fatty ethers are chosen from liquid dialkyl ethers, such as dicaprylyl ether.

The fatty substances may be non-liquid at room temperature and at atmospheric pressure.

The term "non-liquid" preferably means a solid compound or a compound which has a viscosity of greater than 2 Pa·s at a temperature of 25° C. and at a shear rate of 1 $s^{-1}$.

More particularly, the non-liquid fatty substances are chosen from fatty alcohols, fatty acid and/or fatty alcohol esters, non-silicone waxes, silicones or fatty ethers which are non-liquid and preferably solid.

The non-liquid fatty alcohols that are suitable for use in the invention are more particularly chosen from saturated or unsaturated, linear or branched alcohols including from 8 to 30 carbon atoms, which are more preferentially $C_{10}$-$C_{22}$, even more preferentially $C_{14}$-$C_{20}$, better still $C_{16}$-$C_{13}$.

Cetyl alcohol and stearyl alcohol and the mixture thereof (cetylstearyl alcohol) are most particularly preferred.

As regards the non-liquid esters of fatty acids and/or of fatty alcohols, mention may be made notably of solid esters derived from $C_9$-$C_{26}$ fatty acids and from $C_9$-$C_{26}$ fatty alcohols.

Among these esters, mention may be made of octyldodecyl behenate; isocetyl behenate; cetyl lactate; stearyl octanoate; octyl octanoate; cetyl octanoate; decyl oleate; myristyl stearate; octyl palmitate; octyl pelargonate; octyl stearate; alkyl myristates such as cetyl, myristyl or stearyl myristate; hexyl stearate, more particularly myristyl myristate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made notably of: diethyl sebacate; diisopropyl sebacate; diisopropyl adipate; di-n-propyl adipate; dioctyl adipate; dioctyl maleate.

Among all the additional esters mentioned above, it is preferred to use myristyl, cetyl or stearyl palmitates, alkyl myristates such as cetyl myristate, and stearyl myristyl myristate.

The (non-silicone) wax(es) are notably chosen from carnauba wax, candelilla wax, esparto wax, paraffin wax, ozokerite, plant waxes, such as olive tree wax, rice wax, hydrogenated jojoba wax or flower absolute waxes, such as the blackcurrant blossom essential wax sold by the company Bertin (France), or animal waxes, such as beeswaxes or modified beeswaxes (cerabellina); white beeswaxes such as those sold by Koster Keunen; other waxes or waxy raw materials that may be used according to the invention are notably marine waxes, such as the product sold by the company Sophim under the reference M82, polyethylene waxes or polyolefin waxes in general.

The non-liquid silicones in accordance with the invention may be in the form of waxes, resins or gums.

Preferably, the non-liquid silicone is chosen from polydialkylsiloxanes, notably polydimethylsiloxanes (PDMSs), and organomodified polysiloxanes including at least one functional group chosen from poly(oxyalkylene) groups, amino groups and alkoxy groups.

The silicone gums that may be used in accordance with the invention are notably polydialkylsiloxanes and preferably polydimethylsiloxanes with high number-average molecular masses of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products which may be used more particularly in accordance with the invention are mixtures such as:

- mixtures formed from a polydimethylsiloxane with a hydroxy-terminated chain, or dimethiconol (CTFA), and from a cyclic polydimethylsiloxane, also known as cyclomethicone (CTFA), such as the product Q21401 sold by the company Dow Corning;
- mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and a PDMS oil, such as the product SF 1236 from the company General Electric. The product SF 1236 is a mixture of a gum SE 30 defined above, with a viscosity of 20 $m^2/s$ and of an oil SF 96 with a viscosity of $5\times10^6$ $m^2/s$. This product preferably includes 15% of gum SE 30 and 85% of an oil SF 96.

The organopolysiloxane resins that may be used in accordance with the invention are crosslinked siloxane systems containing the following units:

$$R_2SiO_{2/2}, R_3SiO_{1/2}, RSiO_{3/2} \text{ and } SiO_{4/2},$$

in which formulae:

R, which may be identical or different, preferably identical, represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate-type resins notably sold under the names X22-4914, X21-5034 and X21-5037 by the company Shin-Etsu.

Among the additional organomodified silicones, mention may be made of polyorganosiloxanes including:

- substituted or unsubstituted amine groups, for instance the products sold under the names Q2 8220 and Dow Corning 929 or 939 by the company Dow Corning. The substituted amino groups are, in particular, $C_1$-$C_4$ aminoalkyl groups;
- alkoxylated groups, for instance the product sold under the names Abil Wax® 2428, 2434 and 2440 by the company Goldschmidt.

The non-liquid fatty ethers are chosen from dialkyl ethers and notably dicetyl ether and distearyl ether, alone or as a mixture.

The composition according to the invention may comprise one or more butters, which may be identical or different, preferably of plant origin.

According to a preferred mode of the invention, the weight content of $C_{16}$ fatty acid triglycerides, expressed relative to the total amount of fatty acid triglycerides in the butter(s) according to the invention, is less than 23%.

For the purposes of the present invention, the term "butter" (also known as a "pasty fatty substance") means a lipophilic fatty compound which undergoes a reversible solid/liquid change of state and which includes, at a temperature of 25° C. and at atmospheric pressure (760 mmHg), a liquid fraction and a solid fraction. In otherwords, the starting melting point of the pasty compound may be less than 25° C. The liquid fraction of the pasty compound, measured at 25° C., may represent 9% to 97% by weight of the compound. This fraction that is liquid at 25° C. preferably represents between 15% and 85%, more preferably between 40% and 85%, by weight.

Preferably, the butter(s) have an end melting point of less than 60° C.

Preferably, the butter(s) have a hardness of less than or equal to 6 MPa.

Preferably, the pasty fatty substances have, in the solid state, an anisotropic crystal organization, which is visible by X-ray observation.

For the purposes of the invention, the melting point corresponds to the temperature of the most endothermic peak observed on thermal analysis (DSC) as described in the standard ISO 11357-3; 1999. The melting point of a pasty substance or of a wax may be measured using a differential scanning calorimeter (DSC), for example the calorimeter sold under the name DSC Q2000 by the company TA Instruments.

As regards the measurement of the melting point and the determination of the end melting point, the sample preparation and measurement protocols are as follows:

A sample of 5 mg of pasty fatty substance, preheated to 80° C. and withdrawn with magnetic stirring using a spatula that is also heated, is placed in a hermetic aluminum capsule, or a crucible. Two tests are performed to ensure the reproducibility of the results.

The measurements are performed on the calorimeter mentioned above. The oven is flushed with nitrogen. Cooling is performed by an RCS 90 heat exchanger. The sample is then subjected to the following protocol: it is first placed at a temperature of 20° C., and then subjected to a first temperature rise passing from 20° C. to 80° C., at a heating rate of 5° C./minute, then is cooled from 80° C. to −80° C. at a cooling rate of 5° C./minute and finally subjected to a second temperature rise passing from −80° C. to 80° C. at a heating rate of 5° C./minute. During the second temperature rise, the variation of the difference in power absorbed by the empty crucible and by the crucible containing the sample of butter is measured as a function of the temperature. The melting point of the compound is the temperature value corresponding to the top of the peak of the curve representing the variation in the difference in power absorbed as a function of the temperature.

The end melting point corresponds to the temperature at which 95% of the sample has melted.

The liquid fraction by weight of the butter at 25° C. is equal to the ratio of the heat of fusion consumed at 25° C. to the enthalpy of fusion of the butter.

The heat of fusion of the pasty compound is the heat consumed by the compound in order to pass from the solid state to the liquid state. The butter is said to be in the solid state when all of its mass is in crystalline solid form. The butter is said to be in the liquid state when all of its mass is in liquid form.

The heat of fusion of the butter is equal to the integral of the entire melting curve obtained using the abovementioned calorimeter, with a temperature rise of 5 or 10° C./minute, according to the standard ISO 11357-3:1999. The heat of fusion of the butter is the amount of energy required to make the compound change from the solid state to the liquid state. It is expressed in J/g.

The heat of fusion consumed at 25° C. is the amount of energy absorbed by the sample to change from the solid state to the state that it has at 25° C., constituted of a liquid fraction and a solid fraction.

The liquid fraction of the butter measured at 32° C. preferably represents from 30% to 100% by weight of the compound, preferably from 50% to 100%, more preferably from 60% to 100% by weight of the compound. When the liquid fraction of the butter measured at 32° C. is equal to 100%, the temperature of the end of the melting range of the pasty compound is less than or equal to 32° C.

The liquid fraction of the butter measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

As regards the measurement of the hardness, the sample preparation and measurement protocols are as follows:

The composition according to the invention or the butter is placed in a mold 75 mm in diameter, which is filled to about 75% of its height. In order to overcome the thermal history and to control the crystallization, the mold is placed in a Votsch V00018 programmable oven, where it is first placed at a temperature of 80° C. for 60 minutes, then cooled from 80° C. to 0° C. at a cooling rate of 5° C./minute, and then left at the stabilized temperature of 0° C. for 60 minutes, and then subjected to a temperature rise ranging from 0° C. to 20° C., at a heating rate of 5° C./minute, and then left at the stabilized temperature of 20° C. for 180 minutes.

The compression force measurement is taken using a TA/TX2i texturometer from Swantech. The spindle used is chosen according to the texture:

- cylindrical steel spindle 2 mm in diameter for starting materials which are very rigid,
- cylindrical steel spindle 12 mm in diameter for starting materials which are not very rigid.

The measurement involves three steps:

- a first step after automatic detection of the surface of the sample, where the spindle moves at a measuring speed of 0.1 mm/second, and penetrates into the composition according to the invention or the butter to a penetration depth of 0.3 mm, and the software notes the maximum force value reached;
- a second step, known as relaxation, where the spindle remains in this position for one second and the force is noted after 1 second of relaxation; and finally
- a third step, known as withdrawal, where the spindle returns to its original position at a speed of 1 mm/second, and the withdrawal energy of the spindle (negative force) is noted.

The hardness value measured during the first step corresponds to the maximum compression force measured in newtons divided by the area of the texturometer cylinder expressed in $mm^2$ in contact with the butter or the composition according to the invention. The hardness value obtained is expressed in megapascals or MPa.

According to a preferred mode of the invention, the particular butter(s) are of plant origin, such as those described in *Ullmann's Encyclopedia of Industrial Chemistry* ("Fats and Fatty Oils", A. Thomas, published online: Jun. 15, 2000, DOI: 10.1002/14356007.a10_173, point 13.2.2.2. Shea Butter, Borneo Tallow, and Related Fats (Vegetable Butters)).

Mention may be made more particularly of shea butter, Nilotica (*Butyrospermum parkii*) shea butter, galam butter, (*Butyrospermum parkii*), Borneo butter or fat or tengkawang tallow (*Shorea stenoptera*), *shorea* butter, illipe butter, *madhuca* butter or *Bassia madhuca longifolia* butter, mowrah butter (*Madhuca latifolia*), katiau butter (*Madhuca mottleyana*), phulwara butter (*M. butyracea*), mango butter (*Mangifera indica*), murumuru butter (*Astrocaryum murumuru*), kokum butter (*Garcinia indica*), ucuuba butter (*Virola sebifera*), tucuma butter, painya butter (Kpangnan) (*Pentadesma butyracea*), coffee butter (*Coffea arabica*), apricot butter (*Prunus armeniaca*), *macadamia* butter (*Macadamia ternifolia*), grapeseed butter (*Vitis vinifera*), avocado butter (*Persea gratissima*), olive butter (*Olea europaea*), sweet almond butter (*Prunus amygdalus dulcis*), and sunflower butter. Preferentially, the butter(s) according to the invention are chosen from murumuru butter, ucuuba butter, *shorea* butter, illipe butter, shea butter and cupuacu butter, and even more preferentially shea butter.

In one preferred variant of the invention, the weight content of $C_{16}$ fatty acid triglycerides, expressed relative to the total amount of fatty acid triglycerides, ranges from 0 to 22%, better still from 0 to 15% and even better still from 2% to 12%.

The composition according to the invention comprises one or more butters in an amount particularly between inclusively 0.01% and 30% by weight relative to the total weight of the composition, more particularly between inclusively 0.1% and 20% by weight, preferentially between inclusively 0.5% and 10% by weight, and more preferentially between inclusively 1% and 5% by weight.

Preferably, the compositions of the invention contain one or more fatty substances that are liquid at ordinary temperature (25° C.) and at atmospheric pressure (760 mmHg; i.e. $1.013\times10^5$ Pa), optionally combined with one or more fatty substances that are non-liquid under the same conditions.

Preferably, the fatty substance is chosen from a) butters, preferably shea butter;

b) waxes, preferably beeswaxes;

c) non-liquid fatty alcohols, particularly chosen from saturated or unsaturated, linear or branched alcohols including from 8 to 30 carbon atoms, which are preferentially $C_{10}$-$C_{22}$, more preferentially $C_{14}$-$C_{20}$, better still $C_{16}$-$C_{18}$, such as cetyl alcohol and stearyl alcohol and a mixture thereof;

d) non-liquid fatty acid and/or fatty alcohol esters, notably solid esters derived from $C_9$-$C_{26}$ fatty acids and from $C_9$-$C_{26}$ fatty alcohols, in particular alkyl myristates such as cetyl, myristyl or stearyl myristate; hexyl stearate, more particularly myristyl myristate;

e) esters of monoalcohols, at least one from among the alcohol or of the acid from which said esters are derived is branched, such as ethyl palmitate, isopropyl palmitate, alkyl myristates, such as isopropyl myristate or ethyl myristate, isocetyl stearate, 2-ethylhexyl isononanoate, isodecyl neopentanoate, isostearyl neopentanoate and $C_{10}$-$C_{22}$, preferably $C_{12}$-$C_{20}$, alkyl (iso) stearates, such as isopropyl isostearate;

f) cyclic polydialkylsiloxanes including from 3 to 7, preferably from 4 to 5 silicon atoms, such as octamethylcyclotetrasiloxane, decamethylcyclopentasiloxane, dodecamethylcyclopentasiloxane, or cyclohexadimethylsiloxane and also mixtures thereof, preferably cyclohexadimethylsiloxane;

g) oils of plant origin or synthetic triglycerides, such as liquid triglycerides of fatty acids including from 6 to 30 carbon atoms, for instance heptanoic or octanoic acid triglycerides, or alternatively sunflower oil, corn oil, soybean oil, marrow oil, grapeseed oil, sesame seed oil, hazelnut oil, apricot oil, *macadamia* oil, arara oil, sunflower oil, castor oil, avocado oil, caprylic/capric acid triglycerides, jojoba oil, shea butter oil, preferably caprylic/capric acid triglycerides.

The fatty substance(s) used in the composition according to the present invention may be present in the composition in an amount ranging from 1% to 40%, preferably in an amount ranging from 5% to 30% and even more preferentially in an amount ranging from 10% to 20% by weight relative to the total weight of the composition.

vi) the Alkaline Agent(s):

According to a particular embodiment of the invention, the composition of the invention comprises vi) one or more alkaline agents (also called bases). This agent may be chosen from mineral or organic or hybrid alkaline agents, or mixtures thereof.

The mineral alkaline agent(s) are preferably chosen from aqueous ammonia, alkaline carbonates or bicarbonates such as sodium or potassium carbonates and sodium or potassium bicarbonates, sodium hydroxide or potassium hydroxide, or mixtures thereof.

According to an advantageous embodiment of the invention, the alkaline agent(s) are organic amines, i.e. they contain at least one substituted or unsubstituted amino group.

The organic alkaline agent(s) are more preferentially chosen from organic amines with a pKb at 25° C. of less than 12, preferably of less than 10 and even more advantageously of less than 6. It should be noted that it is the pKb corresponding to the function which has the highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds of formula (IV) below:

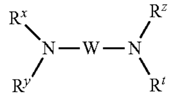

(IV)

in which formula (IV):

W is a divalent $C_1$-$C_6$ alkylene radical optionally substituted with a hydroxyl group or a $C_1$-$C_6$ alkyl radical, and/or optionally interrupted with one or more heteroatoms such as oxygen or $NR^u$;

$R^x$, $R^y$, $R^z$ $R^t$ and $R^u$, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term “alkanolamine” means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and include at least one acid function chosen more particularly from carboxylic acid, sulfonic acid, phosphonic acid and phosphoric acid functions. The amino acids may be in neutral or ionic form.

As amino acids that may be used in the present invention, mention may notably be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function, notably chosen from among histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may notably be made of carnosine, anserine and balenine.

The organic amine is chosen from compounds including a guanidine function. As amines of this type that may be used in the present invention, besides arginine, which has already been mentioned as an amino acid, mention may be made notably of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino)methyl]amino)ethane-1-sulfonic acid.

Mention may be made in particular of the use of guanidine carbonate or monoethanolamine hydrochloride as hybrid compounds.

The composition of the invention preferably contains one or more alkanolamines and/or one or more basic amino acids, more advantageously one or more alkanolamines. Even more preferentially, the organic amine is monoethanolamine.

According to a particular embodiment, the composition of the invention comprises as alkaline agent one or more alkanolamines.

Preferably, the alkanolamine is triethanolamine.

Advantageously, the composition according to the invention has a content of alkaline agent(s) ranging from 0.01% to 10% by weight, preferably from 0.05% to 5% by weight and better still from 0.1% to 1% by weight relative to the weight of said composition.

The Composition

A subject of the invention is a composition comprising:

i) one or more 4-(3-ethoxy-4-hydroxyphenyl)butan-2-one compounds as defined previously;

ii) one or more preserving agents other than i) and/or one or more antioxidants as defined previously, preferably 4-hydroxyacetophenone;

iii) one or more surfactants chosen from nonionic, anionic and zwitterionic surfactants;

iv) one or more thickening polymers which are preferably organic, as defined previously; and v) optionally one or more fatty substances as defined previously.

According to one variant of the invention, the composition comprises:

i) one or more 4-(3-ethoxy-4-hydroxyphenyl)butan-2-one compounds as defined previously;

ii) one or more preserving agents other than i);

iii) one or more surfactants chosen from nonionic, anionic and zwitterionic surfactants;

iv) one or more thickening polymers which are preferably organic, as defined previously; and v) optionally one or more fatty substances as defined previously.

According to one variant of the invention, the composition comprises:

i) one or more 4-(3-ethoxy-4-hydroxyphenyl)butan-2-one compounds as defined previously;

ii) one or more antioxidants as defined previously, preferably 4-hydroxyacetophenone;

iii) one or more surfactants chosen from nonionic, anionic and zwitterionic surfactants;

iv) one or more thickening polymers which are preferably organic, as defined previously; and v) optionally one or more fatty substances as defined previously.

According to yet another variant of the invention, the composition comprises:

i) one or more 4-(3-ethoxy-4-hydroxyphenyl)butan-2-one compounds as defined previously;

ii) one or more preserving agents other than i) and one or more antioxidants as defined previously, preferably 4-hydroxyacetophenone;

iii) one or more surfactants chosen from nonionic, anionic and zwitterionic surfactants;

iv) one or more thickening polymers which are preferably organic, as defined previously; and v) optionally one or more fatty substances as defined previously.

The composition is a physiologically acceptable medium. The composition is in particular a cosmetic or pharmaceutical or dermatological composition. The composition can also be a food (nourishment) composition.

The Physiologically Acceptable Medium:

The term "physiologically acceptable medium" means a medium that is suitable for being applied to keratin materials, also known as a formula support, which is a cosmetic or pharmaceutical medium generally constituted of water or of a mixture of water and one or more organic solvents or of a mixture of organic solvents. Preferably the composition comprises water in a content notably inclusively between 5% and 99.9% relative to the total weight of the composition, more preferentially between 10% and 90% and even more preferentially between 20% and 80% by weight relative to the total weight of the composition.

The Organic Solvents:

The term "organic solvent" means an organic substance that is capable of dissolving another substance without chemically modifying it.

Examples of organic solvents that may be mentioned include a) $C_2$-$C_6$ alkanols, such as ethanol and isopropanol; b) polyols that are miscible with water at room temperature (25° C.), notably chosen from polyols notably containing from 2 to 10 carbon atoms, preferably containing from 2 to 6 carbon atoms, such as glycerol, propylene glycol, 1,3-propanediol, butylene glycol, pentylene glycol, hexylene glycol, dipropylene glycol, diethylene glycol or diglycerol; c) polyol ethers, such as 2-butoxyethanol, propylene glycol monomethyl ether, diethylene glycol monoethyl ether or diethylene glycol monomethyl ether; and also d) aromatic alcohols, such as benzyl alcohol or phenoxyethanol, and mixtures thereof.

According to a particular embodiment, the composition also comprises one or more polyols notably chosen from polyols notably containing from 2 to 10 carbon atoms, preferably containing from 2 to 6 carbon atoms, such as glycerol.

In a preferred embodiment, 4-(3-ethoxy-4-hydroxyphenyl)butan-2-one is used in combination with an effective amount of at least one organic solvent which may be chosen from ethanol, 1,2-propylene glycol, 1,3-propanediol, PEG-8 (polyethylene glycol containing 8 ethylene glycol units), propylene carbonate, dipropylene glycol, 1,2-hexylene glycol, PEG-4.

Preferably, the organic solvent is chosen from ethanol, 1,2-propylene glycol, 1,3-propanediol, PEG-8 and propylene carbonate.

Advantageously, the composition according to the invention comprises 1,3-propanediol, notably in a content ranging from 0.1% to 20% by weight, preferably ranging from 0.1% to 10% by weight and preferentially ranging from 0.5% to 5% by weight, relative to the total weight of the composition.

For the food composition, preference will be given to water and, as organic solvents, to those suitable for consumption, such as ethanol.

The organic solvents are preferably present in proportions preferably inclusively between 0.1% and 40% by weight approximately relative to the total weight of the composition, more preferentially between 1% and 20% by weight approximately and even more particularly inclusively between 5% and 10% by weight relative to the total weight of the composition.

The pH:

The pH of the composition according to the invention is generally inclusively between 2 and 12 approximately and preferably between 3 and 11 approximately. It may be adjusted to the desired value by means of acidifying or alkaline agents usually used in the dyeing of keratin fibers, or alternatively using standard buffer systems.

The pH of the composition is preferentially inclusively between 4.5 and 10, particularly between 6 and 9, more particularly between 7 and 9, and even more particularly around neutral pH 7.

Among the acidifying agents, examples that may be mentioned include mineral or organic acids as defined previously, notably hydrochloric acid, orthophosphoric acid, sulfuric acid, carboxylic acids, for instance acetic acid, tartaric acid, citric acid or lactic acid, and sulfonic acids.

Among the bases or alkaline agents, examples that may be mentioned include aqueous ammonia, alkali metal carbonates, alkanolamines and other alkaline agents as defined below, preferably alkanolamines such as mono-, di- and triethanolamines.

Preferably, the composition comprises i) 4-(3-ethoxy-4-hydroxyphenyl)butan-2-one and also the organic or mineral acid or base salts thereof, and the solvates thereof such as hydrates, in a content ranging from 0.02% to 2% by weight, relative to the total weight of the composition, preferentially ranging from 0.03% to 1% by weight and better still ranging from 0.04% to 0.8% by weight.

A subject of the invention is also a composition comprising, in a physiologically acceptable medium, the antimicrobial mixture described previously.

The term "physiologically acceptable medium" means a medium compatible with human keratin materials such as the skin, the scalp, the nails and keratin fibers such as the hair.

Said medium may comprise one or more additional ingredients, other than the ingredients i) and ii).

The composition may comprise one or more additional ingredients or adjuvants chosen from gelling agents other than the organic thickening polymers as defined previously, non-anionic, cationic, nonionic or zwitterionic, natural or synthetic, film-forming or non-film-forming non-thickening polymers, coloring materials, such as organic or mineral pigments, fragrances, fillers, UV-screening agents, plant extracts, cosmetic and dermatological active agents, and salts.

The composition according to the invention may be in the form of oil-in-water (O/W) emulsions, water-in-oil (W/O) emulsions or multiple emulsions (triple: W/O/W or O/W/O), oily solutions, oily gels, aqueous solutions, aqueous gels, or solid compositions. The composition of the invention is prepared according to the usual methods.

The composition according to the invention preferably comprises water, i.e. it is aqueous. According to one embodiment of the invention, the composition comprises an aqueous phase and an organic or oily phase. Preferably, the composition of the invention is a direct emulsion of the O/W type.

The compositions according to the invention may be more or less fluid and may have the appearance of a white or colored cream, an ointment, a milk, a lotion, a serum, a paste or a foam. They may be optionally applied to the skin in aerosol form. They may also be in solid form, for example in the form of a stick or a compact powder.

The composition according to the invention may notably be in the form of:

- a makeup product, notably for making up the skin of the face, the body, or the lips or the eyelashes;
- an aftershave gel or lotion; a shaving product;
- a deodorant (stick, roll-on or aerosol);
- a hair-removing cream;
- a body hygiene composition such as a shower gel or a shampoo;
- a pharmaceutical composition;
- a solid composition such as a soap or a cleansing bar;
- an aerosol composition also comprising a pressurized propellant;
- a hair-setting lotion, a hair-styling cream or gel, a dyeing composition, a permanent-waving composition, a lotion or a gel for combating hair loss, or a hair conditioner;
- a composition for caring for or cleansing the skin.

The Process for Preparing the Composition:

A subject of the invention is also a process for preparing a composition, in particular a cosmetic or pharmaceutical or food composition, comprising a step of mixing i) 4-(3-ethoxy-4-hydroxyphenyl)butan-2-one, or a base salt or solvate thereof, ii) 4-hydroxyacetophenone or a base salt or solvate thereof, and optionally one or more additional ingredients or adjuvants, notably cosmetic or pharmaceutical or food ingredients or adjuvants, such as those described previously, and optionally water, and one or more organic solvents.

Antimicrobial Activity and Use Thereof:

The antimicrobial activity, notably the synergistic antimicrobial activity, of the mixture i) and ii) according to the invention on fungi, in particular on the species *Candida albicans*, is of value in water treatment. Specifically, fungi represent one of the sources of contamination of water as mentioned in the article "*Fungal contaminants in drinking water regulation? A tale of ecology, exposure, purification and clinical relevance*", Int. J. Environ. Res. Public Health 2017, 14, 636.

The present invention also relates to the use of the antimicrobial mixture in water treatment, in which said water is chosen from domestic or industrial waters, waters from aquatic media, swimming pool/spa waters, and water from air-conditioning systems.

The term "water treatment" refers to a continuous or discontinuous (batch-type) treatment which consists in adding a substance to a water sample to be treated or to a water stream to be treated for the purpose either of preventing the contamination of the water with a contaminant or of partially or totally decontaminating said water to be treated of said contaminant.

Preferably, the water treatment performed in the context of the present invention consists in continuously or discontinuously adding a substance to a sample of water to be treated or to a water stream to be treated in order to partially or totally decontaminate said water to be treated of a contaminant.

The contaminant may be a microorganism, in particular a bacterium and/or a fungus.

Even more preferentially, said water treatment is a treatment of water contaminated with one or more microorganisms, preferably with Gram-positive or Gram-negative bacteria or fungi of the species *Enterococcus faecalis, Candida albicans* or *Pseudomonas aeruginosa.*

The term "waters from aquatic media" means the waters of lakes, tributary rivers, pools, mainstem rivers, sea or ocean bathing areas, underground waters such as well waters and groundwaters, and aquarium waters.

For the purposes of the present invention, the "domestic or industrial waters" comprise waste waters before they have been treated in a purification plant, waters undergoing treatment in a purification plant, waters before they have been treated in a drinking water plant, waters undergoing treatment in a drinking water plant, and also waters circulating in potable or non-potable urban networks, for instance waters circulating in pipes.

The present invention also relates to a continuous or discontinuous water treatment process comprising at least one step of placing a water sample to be treated or a water stream to be treated, said water to be treated being chosen from domestic or industrial waters, water is from aquatic media, swimming pool/spa waters, and waters from air-conditioning systems, in contact with the antimicrobial mixture according to the invention.

Preferably, said step of placing the water to be treated in contact with the antimicrobial mixture according to the invention may in particular be performed by injection in liquid form of said compound, by passage through a filter or a filtering cartridge comprising said compound, or by administration in solid form of said compound in particular in the form of granules, tablets or pellets.

The i) 4-(3-ethoxy-4-hydroxyphenyl)butan-2-one and also the organic or mineral acid or base salts thereof, and the solvates thereof such as hydrates, can be used in a proportion of at least 0.06% by weight, preferably at least 0.1% by weight, even better still at least 0.5% by weight relative to the total weight of water to be treated. In one particular embodiment, the compounds of formula (I) or (I') or the solvates thereof such as hydrates can be used in a proportion of at least 1% by weight relative to the total weight of water to be treated.

The i) 4-(3-ethoxy-4-hydroxyphenyl)butan-2-one and also the organic or mineral acid or base salts thereof, and the solvates thereof such as hydrates, can be used in a concentration ranging from 0.06% tot 10% by weight, preferably preferably from 0.1% to 5% by weight, even better still from 0.5% to 2% by weight relative to the total weight of water to be treated. In one preferred embodiment, the 4-(3-ethoxy-4-hydroxyphenyl)butan-2-one can be used in a concentration ranging from 0.1% to 1% by weight relative to the total weight of water to be treated.

The solvent may be used in a content ranging from 0.05% to 10% by weight relative to the total weight of the water to be treated, preferably ranging from 0.1% to 5% by weight and preferentially ranging from 0.1% to 2.5% by weight relative to the total weight of the water to be treated.

The invention is illustrated in greater detail in the example that follows. The contents of the ingredients are expressed as weight percentages.

EXAMPLES

Example 1: Determination of the Synergistic Antimicrobial Activity as MIC

The demonstration of a synergistic antimicrobial activity effect with a mixture of 4-(3-ethoxy-4-hydroxyphenyl)butan-2-one (referred to as substance A) and of an alcohol compound (referred to as substance B) was performed by calculating the synergy index (or FIC index) according to the following formula:

FIC Index=(CMI de A avec B/CMI de A)+(CMI de B avec A/CMI de B) [Math. 1]

with:

- MIC of A with B: minimum concentration of product A in the combination A+B which makes it possible to obtain an inhibitory effect;
- MIC of B with A: minimum concentration of product B in the combination A+B which makes it possible to obtain an inhibitory effect;
- MIC of A: minimum inhibitory concentration of product A alone;
- MIC of B: minimum inhibitory concentration of product B alone.

This formula was described for the first time in the article by F. C. Kull, P. C. Eisman, H. D. Sylwestrowka, and R. L. Mayer, Applied Microbiology 9:538-541, 1961.

For each compound tested alone, the MIC is considered as the first concentration which makes it possible to obtain a microbial growth percentage of less than or equal to 25%.

As regards the combinations tested, MIC of A with B and MIC of B with A are the respective concentrations of A and of B in the combinations which make it possible to obtain a microbial growth percentage of less than or equal to 25%.

Interpretation of the FIC Index:

When the FIC index value is less than or equal to 1, it is considered that the combination of test compounds has a synergistic effect.

The summary of the results obtained is presented in the following tables.

The combination of compounds A and B, and the compositions containing them, were tested on the following strains or a part thereof: *Aspergillus niger, Escherichia coli, Staphylococcus aureus*, and *Candida albicans.*

The microbial strain *Aspergillus niger* ATCC 6275, and a double-concentration Sabouraud broth liquid culture medium supplemented with polyoxyethylenated (20 OE) sorbitan monopalmitate (Tween 40 from Croda) and Phytagel© BioReagent were used (i.e. a mixture of 5 g of Phytagel+0.6 g Tween 40+60 g of Sabouraud broth).

The microbial strain *Staphylococcus aureus* ATCC 6538 and a double-concentration nutrient broth liquid culture medium were used.

The microbial strain *Candida albicans* ATCC 10231, and a double-concentration Sabouraud broth liquid culture medium were used (i.e. a mixture of 5 g of Phytagel+0.6 g Tween 40+60 g of Sabouraud broth).

A 96-well microplate at an incubation temperature of 32.5° C. is used.

The incubation time of the microplate is:

- from 24 to 30 h under aerobic conditions for microbial *Aspergillus niger* ATCC 6275;
- from 18 to 24 h under aerobic conditions for *Candida albicans* ATCC 10231, *Pseudomonas aeruginosa* ATCC 9027 and *Staphylococcus aureus* ATCC 6538;

Tests

For each compound:

A=compound i) 4-(3-ethoxy-4-hydroxyphenyl)butan-2-one

B=compound ii) preserving agent and/or antioxidant:

B1: 4-hydroxyacetophenone, B2: salicylic acid

Tests of Compounds A and B Alone

50 µl of each of the daughter solutions obtained containing compound A or B are added to the microplate wells. 100 µl of Sabouraud liquid nutrient broth inoculated at double concentration with the *Aspergillus niger* strain and 50 µl of solution are also added thereto.

Tests of Compounds A and B as a Mixture

50 µl of each of the daughter solutions obtained containing compound A and 50 µl of each of the daughter solutions obtained containing compound B are added to the microplate wells. 100 μl of Sabouraud liquid nutrient broth inoculated at double concentration with the strain *Aspergillus niger* are also added thereto.

Microbial Growth Control

A positive microbial growth control was also prepared. The positive microbial growth control corresponds to the mixture of 100 μl of aqueous 1‰ agar solution with 100 μl of Sabouraud liquid nutrient broth inoculated at double concentration with the strain *Aspergillus niger* in the absence of compounds A and B.

Absorbance Control for Compounds A and B Alone

An absorbance control was performed in parallel on compounds A and B alone. This control corresponds to 100 μl of double concentration sterile Sabouraud liquid nutrient broth+100 μl of double concentration compound A or B.

In the three cases (absorbance control, growth control and test), the final volume present in each of the microplate wells is 200 μl.

In the two cases (test and control), the inoculum represents the concentration of the *Aspergillus niger* strain present in the final volume of the wells (200 μl) and is between 2 and $6\times10^5$ cfu/ml of *Aspergillus niger.*

The minimum inhibitory concentration (MIC) of each compound A and B alone and in combination was determined in a known manner by means of optical density measurements at a wavelength of 620 nm.

The test as described above (tests, absorbance control and growth control) was performed again to test the combination A+B on the following strains: *Aspergillus niger, Escherichia coli, Staphylococcus aureus*, and *Candida albicans*

The following results were obtained with compound B1=4-hydroxyacetophenone:

The antimicrobial properties were also evaluated with other compositions, such as those detailed below in table 3 in which the ingredients are given by weight (g) per 100 g of composition. The properties were evaluated at 7 days, 14 days and 1 month.

TABLE 1]

| Ingredients | Composition 1 Invention | Comparative composition 2 | Comparative composition 3 |
|---|---|---|---|
| A ingredient, i) | 0.7 | 0.7 | — |
| B1, ingredient ii) | 0.2 | — | 0.2 |
| Propylene glycol stearate (20 EO), ingredient iii) | 0.8 | 0.8 | 0.8 |
| Glyceryl monostearate/distearate/polyethylene glycol stearate (100 EO) mixture, ingredient iii) | 2 | 2 | 2 |
| Fatty acid (mainly stearic acid) of plant origin, ingredient iii) | 3 | 3 | 3 |
| Acrylamide/sodium acrylamido-2-methylpropanesulfonate copolymer Polysorbate 80/I-C16, ingredient iv) | 2.2 | 2.2 | 2.2 |
| Cetyl alcohol, ingredient v) | 0.5 | 0.5 | 0.5 |
| Stearyl alcohol, ingredient v) | 0.5 | 0.5 | 0.5 |
| Myristyl myristate, ingredient v) | 2 | 2 | 2 |
| White beeswax, ingredient v) | 1 | 1 | 1 |
| Shea butter, ingredient v) | 2 | 2 | 2 |
| Mixture of caprylic and capric acid triglycerides, ingredient v) | 3.1 | 3.1 | 3.1 |
| Isopropyl isostearate, ingredient v) | 1.2 | 1.2 | 1.2 |
| Cyclohexadimethylsiloxane, ingredient v) | 6 | 6 | 6 |
| Glycerol | 7.0 | 7.0 | 7.0 |
| Mineral pigment | 0.15 | 0.15 | 0.15 |

TABLE 1]-continued

| Ingredients | Composition 1 Invention | Comparative composition 2 | Comparative composition 3 |
|---|---|---|---|
| Organic pigment | 0.01 | 0.01 | 0.01 |
| Triethanolamine (basic pH agent) | 0.15 | 0.15 | 0.15 |
| Vitamin E: DL-α-tocopherol | 0.5 | 0.5 | 0.5 |
| Water | qs 100 | qs 100 | qs 100 |

The results on the microbial strain *Escherichia coli* at 7 days are given in the table below:

TABLE 2]

| Compositions | Number of microbes after 7 days |
|---|---|
| Composition 1 (invention) | <200 |
| Composition 2 (comparative) | $2.4\times10^4$ |
| Composition 3 (comparative) | $2.1\times10^5$ |

The results on the microbial strain *Staphylococcus aureus* at 7 and 14 days are given in the table below:

TABLE 3]

| Compositions | Number of microbes after 7 days | Number of microbes after 14 days |
|---|---|---|
| Composition 1 (invention) | $3.7\times10^5$ | $3.4\times10^3$ |
| Composition 2 (comparative) | $2.4\times10^6$ | $9.6\times10^5$ |
| Composition 3 (comparative) | $1.9\times10^6$ | $3.0\times10^4$ |

The results on other microbial strains at 7 days, 14 days and then 1 month are given in the table below:

TABLE 4]

| Compositions/Strains targeted | After 7 days | After 14 days | After 1 month |
|---|---|---|---|
| Composition 1 (invention) | | | |
| *Candida albicans* | $8.6\times10^3$ | <200 | <200 |
| *Aspergillus niger* | $6.8\times10^5$ | $2.0\times10^3$ | <200 |
| Composition 2 (comparative) | | | |
| *Candida albicans* | $2.0\times10^5$ | $8.2\times10^4$ | $3.0\times10^3$ |
| *Aspergillus niger* | $4.1\times10^6$ | $5.0\times10^6$ | $5.4\times10^6$ |
| Composition 3 (comparative) | | | |
| Candida albicans | $3.4\times10^5$ | $1\times10^5$ | $3.8\times10^4$ |
| *Aspergillus niger* | $3.4\times10^6$ | $3.4\times10^6$ | $2.3\times10^6$ |

It is seen from the results in the tables above that the combination of A and 1B1 according to the invention allows a marked antimicrobial improvement, this being after 7 days, 15 days or even one month for a wide variety of microbial strains (*Aspergillus niger, Escherichia coli, Staphylococcus aureus*, and *Candida albicans*).

The following compositions with ii) compound 1B2=salicylic acid were prepared:

TABLE 5]

| Ingredients | Com-position 4 Invention | Com-parative composition 5 |
|---|---|---|
| A, ingredient i) | 0.7 | 0.7 |
| B2, ingredient ii) | 0.2 | 0.2 |
| Propylene glycol stearate (20 EO), ingredient iii) | 0.8 | 0.8 |
| Glyceryl monostearate/distearate/polyethylene glycol stearate (100 EO) mixture, ingredient iii) | 2 | 2 |
| Stearic acid, ingredient iii) | 3 | — |
| Dipalmitoylethylhydroxyammonium methosulfate (30% by weight) and cetearyl alcohol | — | 3 |
| Acrylamide/sodium acrylamido-2-methylpropanesulfonate copolymer Polysorbate 80/I-C16, ingredient iv) | 2.2 | 2.2 |
| Cetyl alcohol, ingredient v) | 0.5 | 0.5 |
| Stearyl alcohol, ingredient v) | 0.5 | 0.5 |
| Myristyl myristate, ingredient v) | 2 | 2 |
| White beeswax, ingredient v) | 1 | 1 |
| Shea butter, ingredient v) | 2 | 2 |
| Mixture of caprylic and capric acid triglycerides, ingredient v) | 3.1 | 3.1 |
| Isopropyl isostearate, ingredient v) | 1.2 | 1.2 |
| Cyclohexadimethylsiloxane, ingredient v) | 6 | 6 |
| Glycerol | 7.0 | 7.0 |
| Mineral pigment (mica) | 0.15 | 0.15 |
| Organic pigment | 0.01 | 0.01 |
| Triethanolamine (pH 6.4 agent) | 0.35 | 0.28 |
| Vitamin E: DL-α-tocopherol | 0.5 | 0.5 |
| Water | qs 100 | qs 100 |

It is seen that comparative composition 5 comprising a cationic surfactant is much less stable than composition 4 according to the invention. In addition, the viscosity of composition 4 according to the invention is 32.5 poises, whereas comparative composition 5 is much more viscous, since its viscosity is 51.5 poises. These viscosity values were measured at 25° C. and at atmospheric pressure.

Other Comparative Tests:

The following two compositions were prepared; the amounts of the ingredients are given in g per 100 g of composition:

TABLE 6

| Ingredients | Com-parative composi-tion 6 | Com-position 7 invention |
|---|---|---|
| Sorbitan tristearate (Span 65 V from Croda) (ingredient iii) | 0.9% | 0.9% |
| Mixture of glyceryl monostearate/distearate (36/64)/potassium stearate (Tegin Pellets from Goldschmidt) (ingredient iii) | 3% | 3% |
| Polyethylene glycol stearate (40 ethylene oxide units - 40 EO) (ingredient iii) | 2% | 2% |
| 4-(3-Ethoxy-4-hydroxyphenyl)butan-2-one - EZ (ingredient D | 0.05% | 0.05% |
| Phenoxyethanol (ingredient ii) | 0.2% | 0.2% |
| Caffeine (ingredient ii) | 0.1% | 0.1% |
| 1,3-Propanediol | 3% | 3% |
| Mixture of liquid petroleum jelly (mineral oil), microcrystalline wax and paraffin (Vaseline Blanche Codex 236 from Aiglon) (ingredient v) | 4% | 4% |
| Stabilized shea olein (Shea Olein from Olvea) (ingredient v) | 1% | 1% |

TABLE 6-continued

| Ingredients | Com-parative composi-tion 6 | Com-position 7 invention |
|---|---|---|
| Cyclopentadimethylsiloxane (ingredient v) | 5% | 5% |
| Cetyl alcohol (ingredient v) | 4% | 4% |
| Apricot kernel oil (ingredient v) | 0.3% | 0.3% |
| Hydrogenated polyisobutene (Parleam from NOF Corporation) | 2% | |
| Acrylamide/sodium acrylamido-2-methylpropanesulfonatecopolymer Polysorbate 80/I-C16 (ingredient iv) | — | 2% |
| Myristyl myristate (ingredient v) | 2% | 2% |
| Stearic acid (ingredient iii) | 1.2% | 1.2% |
| Citric acid | 0.2% | 0.2% |
| Glycerol | 3% | 3% |
| Sodium hydroxide | 0.05% | 0.05% |
| Water | qs 100 | qs 100 |

The composition according to the invention is glossy, aerated, white, with a "base" odor.

Microscopic Evaluation of the Compositions:

It is seen under a microscope in white light, with a magnification of ×400 (Leica DM2500 with Archimed Microvision software) that comparative composition 6 comprises vacuoles, whereas composition 7 according to the invention is more structured, with no visible vacuoles, making it more stable.

Sensory Evaluation:

The application of composition 7 of the invention is fresher, easier, more viscous and applies better, with a pleasant sensation by rotation of the fingers on the skin for significantly longer than that obtained with composition 6.

It is also seen after application of composition 7 according to the invention to the skin, and a much more matt and soft-focus appearance than that obtained with comparative composition 6.

Measurement of the Soft Focus/Matt Effect on Keratin Materials:

To measure the transmittance, the haze and the brightness, use was made of a Byk hazemeter, model: HazeGard Plus.

The matt effect/soft focus results after application to the skin, judged by a panel of evaluators, are corroborated with the transmittance, haze, brightness and gloss measurements. To quantify the transmitted light of a formulation and also its soft focus capacity, the "haze" parameters are measured. The haze measurement consists in determining the amount of light rays deviated from their trajectory by the sample. It makes it possible to quantify the soft-focus power of the material.

Study conditions: Room temperature: 25° C., film drying temperature: 25° C., film drying time: 1 h.

Elcometer spreader, model: 4340—A transparent 100 micron sheet is placed on the spreader, adjusted to a thickness in position of 25 microns, the sample is then added and the film is then left to dry for 1 hour at room temperature. The transparent sheet onto which the sample 25 microns thick is spread is then placed on the lenses of the apparatus and the H (haze) and B (brightness) values are measured.

To measure the gloss, use is made of a Byk glossmeter, model: Micro TRI gloss. The spreading is identical to that described above, with a measurement being taken directly using a transparent sheet placed on a black surface and the glossmeter.

TABLE 7]

| Observations/measurements | Comparative composition 6 | Composition 7 Invention |
|---|---|---|
| Haze | 22.77 | 53.28 |
| Brightness | 48.15 | 12.15 |
| Sheen | 40.32 | 18.65 |

It is seen from the results of table 7 that the composition according to the invention, composition 7, makes it possible to significantly improve the soft-focus and matt effect relative to the comparative composition.

The invention claimed is:

1. A mixture comprising:

i) one or more 4-(3-ethoxy-4-hydroxyphenyl) butan-2-one compounds or one or more organic or mineral base salts thereof, solvates thereof or mixtures thereof;

ii) one or more preserving agents other than i) chosen from organic preserving agents bearing aromatic groups, and optionally one or more antioxidants;

iii) one or more nonionic surfactants and one or more anionic surfactants;

iv) one or more organic non-associative thickening polymers; and optionally v) one or more fatty substances;

wherein when the mixture comprises one or more cationic surfactants, they are in an amount of less than 0.5% by weight relative to the total weight of i) to v);

wherein i) is present in the mixture in an amount of 0.06% to 10% by weight relative to the total weight of i) to v); i) and ii) are present in amounts such that the weight ratio i)/ii) ranges from 0.05 to 5; the one or more nonionic surfactants are present in the mixture in an amount of 0.5% to 20% by weight relative to the total weight of i) to v), one or more anionic surfactants are present in the mixture in an amount of 0.5% to 20% by weight relative to the total weight of i) to v); the total weight of one or more nonionic surfactants and one or more anionic surfactants is 1% to 30% by weight relative to the total weight of i) to v); one or more organic non-associative thickening polymers are present in the mixture in an amount of 0.01% to 10% by weight relative to the total weight of i) to v); i), ii), iii) and iv) and optionally v) comprise 80% to 90% by weight relative to the total weight of the mixture, and the mixture has a viscosity of less than 90 poises.

2. The mixture as claimed in claim 1, in which the weight ratio i)/ii) ranges from 0.08 to 5.

3. The mixture as claimed in claim 1, in which the preserving agent(s) ii) are chosen from a) benzene-based carboxylic acids which are optionally substituted on the phenyl group with one or more groups chosen from hydroxyl, $(C_1-C_{10})$alkyl and $(C_1-C_{10})$alkylcarbonyl, and the base salts thereof, b) hydroxybenzoic acid esters optionally substituted on the phenyl group with one or more groups chosen from $(C_1-C_{10})$alkyl, and c) aromatic alcohols.

4. The mixture as claimed in claim 1, in which ii) further comprises one or more antioxidants.

5. The mixture as claimed in claim 1, in which ii) is or are chosen from 4-hydroxyacetophenone, the salts thereof, and the solvates thereof.

6. A composition comprising the mixture of ingredients i), ii), iii) and iv) and optionally v) as defined in claim 1, wherein the composition comprises an amount of cationic surfactants of less than 0.2% by weight.

7. The composition as claimed in claim 6, which comprises 1% to 10% by weight relative to the total weight of i) to v) of the one or more nonionic surfactants and 1% to 10% by weight relative to the total weight of i) to v) of the one or more anionic surfactants.

8. The composition as claimed in claim 6, which comprises one or more nonionic surfactants chosen from: (poly) ethoxylated fatty alcohols; glycerolated fatty alcohols; alkylpolyglycosides or a mixture thereof.

9. The composition as claimed in claim 6, which comprises one or more anionic surfactants chosen from: alkyl carboxylic acids, alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, salts of alkyl diesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts, and the corresponding non-salified forms of all these compounds, the alkyl and acyl groups of all these compounds including from 8 to 30 carbon atoms.

10. The composition as claimed in claim 6, in which the amount of surfactants ranges from 2% to 10% by weight relative to the total weight of the composition of the invention.

11. The composition as claimed in claim 6, which comprises one or more fatty substances chosen from:

a) butters;

b) waxes;

c) non-liquid fatty alcohols;

d) non-liquid fatty acid and/or fatty alcohol esters;

e) esters of monoalcohols, at least one from among the alcohol or of the acid from which said esters are derived is branched;

f) cyclic polydialkylsiloxanes including from 3 to 7; and g) oils of plant origin or synthetic triglycerides.

12. The composition as claimed in claim 6, which comprises one or more fatty substances in an amount ranging from 1% to 40% by weight relative to the total weight of the composition.

13. The composition as claimed in claim 6, wherein the one or more organic non-associative thickening polymers are chosen from crosslinked acrylic acid or methacrylic acid homopolymers or copolymers, crosslinked 2-acrylamido-2-methylpropanesulfonic acid homopolymers and crosslinked or non-crosslinked acrylamide copolymers thereof, ammonium acrylate homopolymers, or copolymers of ammonium acrylate and of acrylamide and mixtures thereof.

14. The composition as claimed in claim 6, which comprises one or more thickening organic polymers resulting from the (co)polymerization:

of acrylate monomer $CH_2{=}C(R')-COOR'''$ (VIa) and/or of acrylamide monomer $CH_2{=}C(R')-CO-N(R'')-LY^-M$ (VIb)

in which formulae (VIa) and (VIb):

R' and R'', which may be identical or different, represent a hydrogen atom or a $(C_1-C_6)$alkyl group, R''' represents an alkali metal, an alkaline-earth metal, a hydrogen atom or a ($C_1$-$C_6$)alkyl group optionally substituted with one or more hydroxyl, carboxyl or amino groups;

L representing a linear or branched, saturated or unsaturated, cyclic or acyclic, divalent hydrocarbon-based group optionally interrupted and/or substituted with one or more heteroatoms and comprising from 1 to 20 carbon atoms $Y^-$ represents an anionic group.

15. The composition as claimed in claim 6, which comprises one or more thickening organic polymers bearing sugar units.

16. The composition as claimed in claim 6, which comprises one or more thickening organic polymers in a content ranging from 0.1% to 5% by weight relative to the total weight of the composition.

17. The composition as claimed in claim 6, which comprises one or more fatty substances chosen from a) butters; b) waxes; c) non-liquid fatty alcohols; d) non-liquid fatty acid and/or fatty alcohol esters; e) esters of monoalcohols, at least one from among the alcohol or of the acid from which said esters are derived is branched; f) cyclic polydialkylsiloxanes including from 3 to 7, and wherein ii) is chosen from 4-hydroxyacetophenone, the salts thereof, and the solvates thereof, the fatty substance/surfactant(s) weight ratio of which is inclusively between 5 and 20.

18. The composition as claimed in claim 6, which comprises one or more fatty substances chosen from a) butters; b) waxes; c) non-liquid fatty alcohols; d) non-liquid fatty acid and/or fatty alcohol esters; e) esters of monoalcohols, at least one from among the alcohol or of the acid from which said esters are derived is branched; f) cyclic polydialkylsiloxanes including from 3 to 7, wherein the weight ratio of the fatty substance/sum of surfactant(s) and polymer(s) [surfactant(s)+polymer] of which is inclusively between 0.8 and 10.

19. The composition as claimed in claim 6, which comprises an aqueous phase and an organic or oily phase.

20. The composition as claimed in claim 6, which comprises one or more organic solvents.

21. The composition as claimed in claim 6, which comprises one or more organic solvents present in amounts inclusively between 0.1% and 40% by weight relative to the total weight of the composition.

22. A non-therapeutic cosmetic treatment process, comprising the application to said keratin materials of a composition as claimed in claim 6.

23. A process for preserving a composition comprising a physiologically acceptable medium incorporating into said composition an antimicrobial mixture as defined in claim 1 or a composition thereof.

* * * * *